(12) United States Patent
Goede

(10) Patent No.: US 10,650,115 B2
(45) Date of Patent: May 12, 2020

(54) PROCESSING, AGGREGATING, ANNOTATING, AND/OR ORGANIZING DATA

(71) Applicant: XIFIN, Inc., San Diego, CA (US)

(72) Inventor: Patricia Goede, Salt Lake City, UT (US)

(73) Assignee: XIFIN, Inc., San Diego, CA (US)

( * ) Notice: Subject to any disclaimer, the term of this patent is extended or adjusted under 35 U.S.C. 154(b) by 467 days.

(21) Appl. No.: 15/056,817

(22) Filed: Feb. 29, 2016

(65) Prior Publication Data

US 2016/0253456 A1 Sep. 1, 2016

Related U.S. Application Data

(60) Provisional application No. 62/126,206, filed on Feb. 27, 2015.

(51) Int. Cl.
*G16H 30/00* (2018.01)
*G06F 19/00* (2018.01)
*G06F 16/58* (2019.01)
*G16H 30/40* (2018.01)
*G16H 30/20* (2018.01)

(52) U.S. Cl.
CPC ........ *G06F 19/321* (2013.01); *G06F 16/5866* (2019.01); *G16H 30/00* (2018.01); *G16H 30/20* (2018.01); *G16H 30/40* (2018.01)

(58) Field of Classification Search
CPC ............ G06F 19/321; G06F 17/30598; G06F 17/30268; G16H 30/00; G16H 30/40; G16H 30/20

USPC ............................................................ 705/3
See application file for complete search history.

(56) References Cited

U.S. PATENT DOCUMENTS

| | | | | |
|---|---|---|---|---|
| 3,599,161 A * | 8/1971 | Stoughton | .......... | G01R 31/3193 714/32 |
| 7,453,472 B2 * | 11/2008 | Goede | ................... | G06F 40/169 345/634 |
| 9,208,381 B1 * | 12/2015 | Shanmugasundaram | | ..................... H04L 67/22 |
| 2006/0020493 A1 * | 1/2006 | Cousineau | ............. | G06Q 50/22 705/2 |
| 2010/0257189 A1 * | 10/2010 | Campbell | ............... | G06Q 10/10 707/758 |
| 2013/0211230 A1 * | 8/2013 | Sperling | ................ | A61B 8/468 600/410 |
| 2014/0108460 A1 * | 4/2014 | Casella dos Santos | | ..................... G06F 16/35 707/794 |

* cited by examiner

*Primary Examiner* — Robert A Sorey
*Assistant Examiner* — Kimberly A. Sass
(74) *Attorney, Agent, or Firm* — Maschoff Brennan

(57) ABSTRACT

The present disclosure is related to processing, aggregating, and/or organizing data. A system may include a processor configured to process input data and identify a relationship amongst received input data in a data set. The system may also include an aggregator coupled to the processor and configured to receive processed data from the processor and aggregate data within the data set while maintaining one or more data relationships within the data set. Further, the system may include an annotation service module coupled to the aggregator and configured to generate at least one annotation that is maintained across at least a portion of the data within the data set.

14 Claims, 19 Drawing Sheets

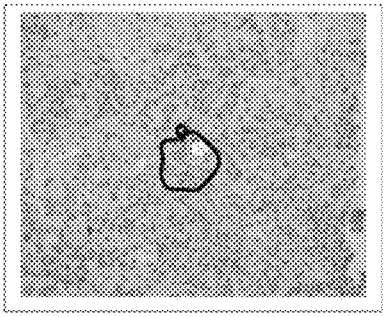
PR- Negative 10X Mag

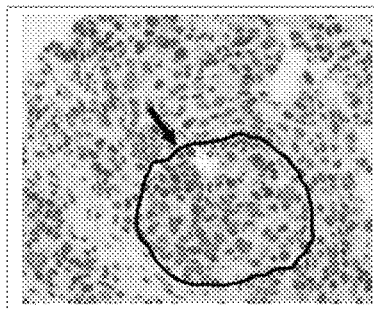
ER-Negative 20X Mag

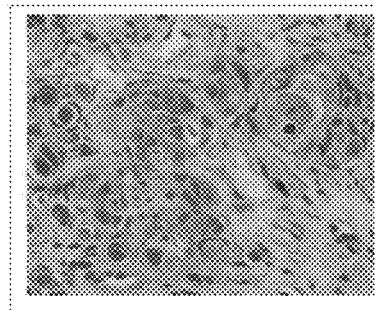
HER2- Negative 40X Mag

FINDINGS: HPI: 59 y/o female who in Nov 2012 was found to have two breast masses in the right breast. One in the 8:00 position and one in the 8-9:00 position. The 9:00 mass was biopsied and showed fibrotic tissue. Right breast- UOQ 3.4 cm palpable mass, possible palpable LN right axilla. Left breast- no palpable masses. Family History: Non-contributory. Patient was told both biopsies were benign so she did not seek treatment.
CLINICAL HISTORY: Prior Reduction Mammoplasty, GERD; Medications: Nexium, Combipatch - discontinued

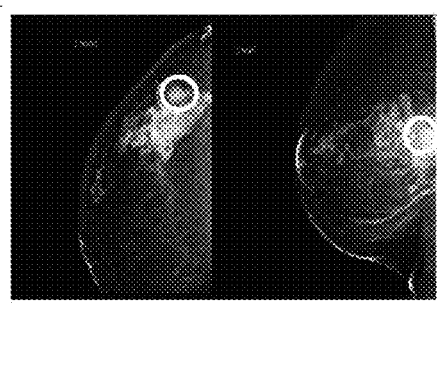
Digital Mammography – mass in Right breast

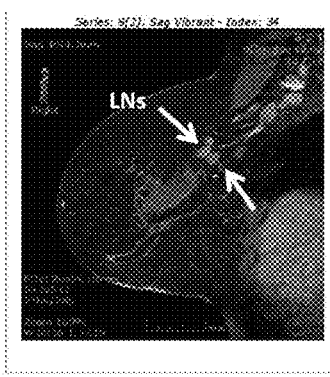
Breast MRI showing affected lymph nodes

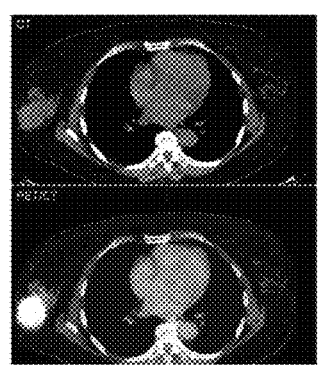
Axial 18F-FDG PET and fused PET/CT uptake

*FIG. 11*

Focus on Dermatopathology: Skin Cancer Quality System

| Quality Measure | Quality Domain | Description | Notes/Comments |
|---|---|---|---|
| Screening for Disease- where images are used for screening | | | |
| ***PQRS 26 | Effective Clinical Care | Melanoma Complete Physical Skin Examination document that certain parameters are in the system. Could be an encounter | Documentation by Photos to measure changes over time. Generated in the physician's office |
| ***PQRS 27 | Effective Clinical Care | Self-examination counseling for the patient. List that is updated with version information from the cancer society. | Develop Packet for Patient |
| Subtype of Disease | | | |
| QOPI 1 | ASCO Guideline and State Law | Pathology Report to confirm pathologic diagnosis. Contains: demographics 1) gender/sex, 2) race/ethnicity, 3) DOB, 4) Identifiers, 5) molecular, cellular, histologic, and genetic results | From all EMRs where Pathology is originally read |
| Stages of Disease | | | |
| PQRS 194 Claims, Registry, Measure Group (Oncolgy) | Effective Clinical Care | Oncology: Cancer Stage Documented: Percentage of patients, regardless of age, with a diagnosis of cancer who are seen in the ambulatory setting who have a baseline American Joint Committee on Cancer (AJCC) cancer stage or documentation that the cancer is metastatic in the medical record at least once during the 12 month reporting period | |
| Supervision of Disease (with curative or non-curative intent) document that you follow for a minimum of 25 years | | | |
| PQRS 138 | Communication and Care Coordination | Melanoma: Coordination of Care: Percentage of patient visits, regardless of age, with a new occurrence of melanoma who have a treatment plan documented in the chart that was communicated to the physician(s) providing continuing care within one month of diagnosis | Registry available with the historical record |
| PQRS 25 | Effective Clinical Care | Melanoma: Patient Medical History | Summation of items QOPI #1 PQRS 194 & 138 |
| Surveillance of Disease (with partial or complete response) document that you follow for a minimum of 25 years | | | |
| PQRS 137 AMAPCPI/NCQA Federal Measure | Effective Clinical Care | Melanoma: Continuity of Care- Recall System: Percentage of patients, regardless of age, with a current diagnosis of melanoma or a history of melanoma whose information was entered, at least once within a 12 month period, into a recall system that includes: *A target date for the next complete physical skin exam, AND *A process to follow up with patients who either did not make an appointment within the specified timeframe or who missed a scheduled appointment | Reminders (notifiers) for the primary care physician, dermatologist or oncologist. Recall system to document the moles and other skin items |
| ***PQRS 224 | Efficiency and Cost Reduction | Melanoma: Overutilization of Imaging Studies in Melanoma: Percentage of patients, regardless of age, with a current diagnosis of stage 0 through IIC melanoma or a history of melanoma of any stage, without signs or symptoms suggesting systemic spread, seen for an office visit during the one-year measurement period, for whom no diagnostic imaging studies were ordered | Count and document every imaging study that has been conducted per year. Proof that you are not conduction too many imaging studies |

FIG. 12

PROCESSING, AGGREGATING, ANNOTATING, AND/OR ORGANIZING DATA

CROSS-REFERENCE TO RELATED APPLICATIONS

This application claims the benefit of and priority to U.S. Provisional App. No. 62/126,206, filed Feb. 27, 2015, which is incorporated herein by reference.

TECHNICAL FIELD

This disclosure relates generally to processing data, aggregating data, annotating data, organizing data, or any combination thereof. Yet more specifically, this disclosure relates to establishing and maintaining data relationships within data sets including data from various data sources. Even more specifically, this disclosure relates to image annotation and establishing and maintaining data relationships across various imaging modalities and specialties.

BACKGROUND

It is common practice to include annotations (e.g., metadata) with an image (e.g., a digital image) to convey information in a human-readable format as well as structured information that can be consumed by an external system. More specifically, annotations, such as, a region of interest, straight line, arrow, measurement results, graphical patterns, characters, and symbols, may be displayed in or near a visible image.

Conventional imaging systems, which may lack context, are complicated due to data residing in disparate systems from which it is generated, especially when the images are accessed by geographically disconnected users. Conventionally, images and related text from a single specialty (e.g., single modality) are maintained in separate systems and are not maintained in a single collection for use in decision-making. Tools for conveying important information and for linking images from one modality to images from a different modality do not exist. Moreover, systems and methods for joining specific areas of interest with annotated regions of interest from individual images from the different modalities do not exist.

While there are standards that define how images are generated for different individual specialties and modalities, standards that aggregate and maintain relationships between such images and related textual information in a human and/or machine-readable format do not exist.

The subject matter claimed herein is not limited to embodiments that solve any disadvantages or that operate only in environments such as those described above. Rather, this background is only provided to illustrate one example technology area where some embodiments described herein may be practiced.

BRIEF SUMMARY

According to one embodiment of the present disclosure, a system may include a processor configured to process input data and identify a relationship amongst input data in a data set. The system may also include an aggregator coupled to the processor and configured to receive processed data from the processor and aggregate data within the data set while maintaining one or more data relationships within the data set. Further, the system may include an annotation service module coupled to the aggregator and configured to generate at least one annotation that is maintained across at least a portion of the data within the data set.

According to others embodiments, the present disclosure includes methods for processing, aggregating, annotating and/or organizing data. Various embodiments of such a method may include receiving a plurality of data inputs. The method may also include establishing one or more data sets including the plurality of data inputs, wherein one or more data inputs in each data of the one or more data set shares a common identifier. Further, the method may include maintaining relationships amongst data inputs in each data set of the one or more data sets. The method may also include generating one or more outputs based on data in a data set of the one or more data sets.

Yet other embodiments of the present disclosure comprise computer-readable media storage storing instructions that when executed by a processor cause the processor to perform instructions in accordance with one or more embodiments described herein.

Other aspects, as well as features and advantages of various aspects, of the present disclosure will become apparent to those of skill in the art through consideration of the ensuing description, the accompanying drawings and the appended claims.

BRIEF DESCRIPTION OF THE DRAWINGS

FIG. 11 depicts an example output, in accordance with an embodiment of the present disclosure.

FIG. 12 depicts an example output table, according to an embodiment of the present disclosure

DETAILED DESCRIPTION

Referring in general to the accompanying drawings, various embodiments of the present disclosure are illustrated to show the structure and methods for image annotation systems and devices. Common elements of the illustrated embodiments are designated with like numerals. It should be understood that the figures presented are not meant to be illustrative of actual views of any particular portion of the actual device structure, but are merely schematic representations which are employed to more clearly and fully depict embodiments of the disclosure.

The following provides a more detailed description of the present disclosure and various representative embodiments thereof. In this description, functions may be shown in block diagram form in order not to obscure the present disclosure in unnecessary detail. Additionally, block definitions and partitioning of logic between various blocks is exemplary of a specific implementation. It will be readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

Figure 1:
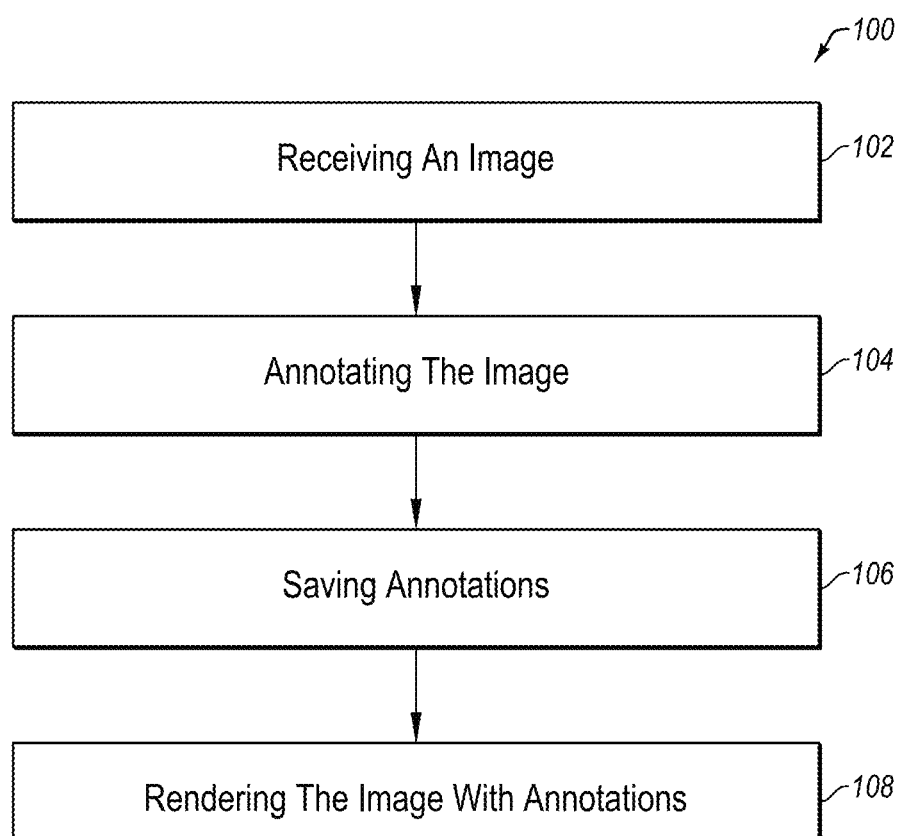
FIG. 1 is a flowchart depicting a method, in accordance with an embodiment of the present disclosure.

FIG. 1 illustrates a method for annotating a digital image with vector annotations. As illustrated, method 100 includes receiving an image (depicted by act 102) to annotate. The image may include a raster based image (e.g., a bitmap image) and may be an image stored in one of many available formats such as, for example, a JPEG, a BMP, a PNM, a PNG, a TIFF, and a PPM. The image, which may be retrieved from a storage medium, may include a scanned image, a digital photograph, a work created on a computer (e.g., such as an architectural drawing), computed tomography, magnetic resonance image or any other valid source for a digital image. The image can be in a two dimensional or a three dimensional format.

Method 112 may further include annotating the image (depicted by act 104). As will be appreciated, an annotation may include, for example, a region of interest, a pointer, textual information, or any combination thereof. A visible portion of the annotation may include, for example, the region of interest, the pointer, and the symbol. For example, in the medical field, a region of interest could be a feature or structure on an image (e.g., pathology, tumor, nerve) that conveys a clinical or research finding. Typically, a point, line, or polygon may be generated to indicate a region of interest. A pointer may be defined by an author and may be partially based on a computer depending on where the author initially places the pointer. For example, the author may select where a tail of the pointer should be positioned, and an algorithm may calculate the closest point on the region of interest to place a tip of the pointer. This method may enable the author to determine the layout of visual information on the image, without relying entirely automated process, which may be unpredictable.

Textual information, which may include, for example, text, a symbol, a label, a caption, or any combination thereof, may enable the author to add knowledge on contents of an image. As will be appreciated, a symbol may be drawn on an image without obscuring visual information or interfering with other annotations. Further, a symbol may be used to link visual annotation to textual information. In one example, a symbol may comprise a lexicon specific piece of textual information enabling the annotation to be linked to a larger body of information (e.g., outside the image). A label may include word or phrase that defines the visual annotation. A label may be derived from a lexicon or vocabulary, enabling dictionary-style lookup (e.g., via software). Lexicon-specific textual information and/or symbols may be linked to a larger body of information outside the image. A caption, which may include, one or more words, may describe the annotation.

Throughout an annotation process, one or more authors may determine presentation attributes, which define how annotations may be drawn when rendered. Visible parts of presentation attributes (e.g., font, size, color, pointer type, and tip location) may also be interpreted differently depending on the medium (e.g. laser printer, journal article or web browser). Further, presentation attributes may include numerous options to provide enhanced control over a presentation and annotation reuse.

For example, annotation size attributes may include "small," "default" and "large." This option may control a size of a pointer and associated text rendered with a visual annotation. Annotation color attributes may include, for example, "light," "default" and "dark." As will be understood, this option may control the color of a region of interest (e.g., a polygon), a pointer, and any text, which may be rendered as part of an annotation. Pointer type attributes may include, for example, "spot," "line," "pin," "arrow" and "arrowhead." Details (e.g., appearance of pointers) may be controlled via a style sheet and rendering software. Further, pointer tip attributes, which may comprise, for example, "center" and "edge," may control where a tip of a pointer appears (i.e., relative to the region of interest). Using the pointer tip attributes, an actual pixel location of a pointer tip may be determined. Other embodiments may utilize free form placement of a pointer and/or a pointer tip.

Method 100 further includes saving one or more annotations (depicted by act 106). The one or more annotations may be saved as vector information, which is linked to the image. The vector information may be saved inside the image file or as a separate file. As will be appreciated, some image formats (e.g., PNG) allow the vector information to be saved inside of the image file. Saving annotations, and possibly metadata, as vector information may allow the annotations to be re-drawn or scaled and, thus, the presentation may be improved. In addition, the annotations may be modified for various reasons, such as, for example, to create interactive presentations.

As will be appreciated, annotations and metadata may be saved inside an image file with actual image information. Metadata may include any information about the image or annotations, such as author name, including the date and time that the annotations were performed, the names of persons who have viewed the image or annotations, including and the date and time of the viewing. In a specific example related to medical images, metadata may include patient information.

An annotation may also be stored in a separate file (i.e., apart from, but related to, the image). The text information may or may not be automatically displayed (i.e., may or may not be visually hidden as a default by an image viewer). It is noted that the text information may be accessible for publishing, cataloging, displaying (e.g., interactive display), and annotation drawing. As will be appreciated, storing text information (e.g., metadata and vector-based annotations) inside the image file, may link the text information with the image information.

It is noted that the vector information can be stored in any format, such as in, for example only, extensible Markup Language ("XML") format. It will be understood, storing the vector information in the XML format may ensure that annotations remain accessible as vector data (i.e., not embedded in an image), allow the annotations and images to become re-usable, and maintain linkage between the annotations and images. Further, management of multiple versions in a proprietary format or distribution of multiple copies of the same image may not be necessary. It is further noted that an output is not platform specific. In one example, a Scalable Vector Graphics ("SVG") output format, which is an extension of the XML specification, may be used. Using SVG may provide for reuse, interactivity, and extensibility, interactive web viewing, and reuse. In addition, using SVG may enable the annotations and visual expert knowledge (i.e., labels and captions) to remain linked to the image.

Method 100 further includes rendering the image with the one or more annotations (e.g., for display via an electronic display device) (depicted by act 108). It is noted that embodiments of the present disclosure may be configured for cross-media distribution. Stated another way, embodiments described herein may enable annotated images to be converted from one form of media to another form of media.

Figure 2:
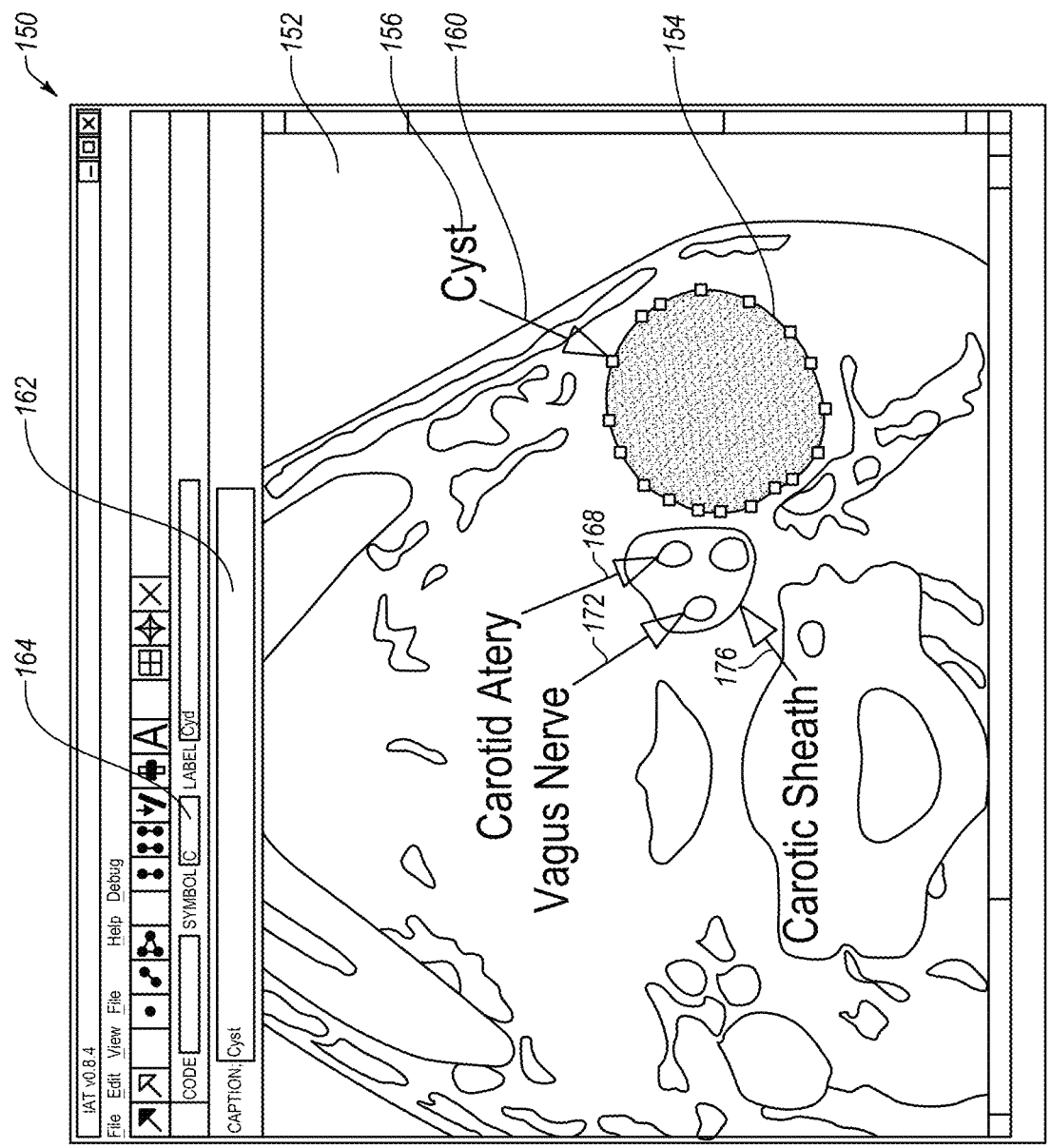
FIG. 2 is a depiction of a display showing various features of an embodiment of the present disclosure.

With reference to FIG. 2, a display 150 including an image 152 and annotations is depicted. More specifically, display 150 includes several regions of interest associated with image 152. One region of interest, as indicated by reference numeral 154, is noted by a label 156 (i.e., "Cyst"), which is connected to region of interest 154 by a pointer 160. In addition, display 150 includes a caption 162 and a symbol 164 for region of interest 154. Display 150 also includes label (i.e., "Carotid Artery") connected to the depicted carotid artery via pointer 168, a label (i.e., "Vagus Nerve") connected to the depicted vagus nerve via a pointer 172, and a label (i.e., "Carotic Sheath") connected to the depicted carotid sheath via a pointer 176. As will be appreciated, the annotations are useful in conveying information to an observer.

In accordance with an embodiment of the present disclosure, a separate annotation file may contain a digital signature of the image file in case the two files are separated. As will be explained in greater detail below, reuse of the image is facilitated since the original image remains unchanged and the annotations remain linked to the image. It will be appreciated that because the annotations are not embedded into the image, they can be referenced, grouped (as shown in FIG. 2) and indexed for a variety of purposes. In addition, while multiple annotations can be added to an image, not all of the annotations need be displayed at the option of the presenter, to create a context appropriate annotated image. These multiple annotations can be interactive.

Figure 3A:
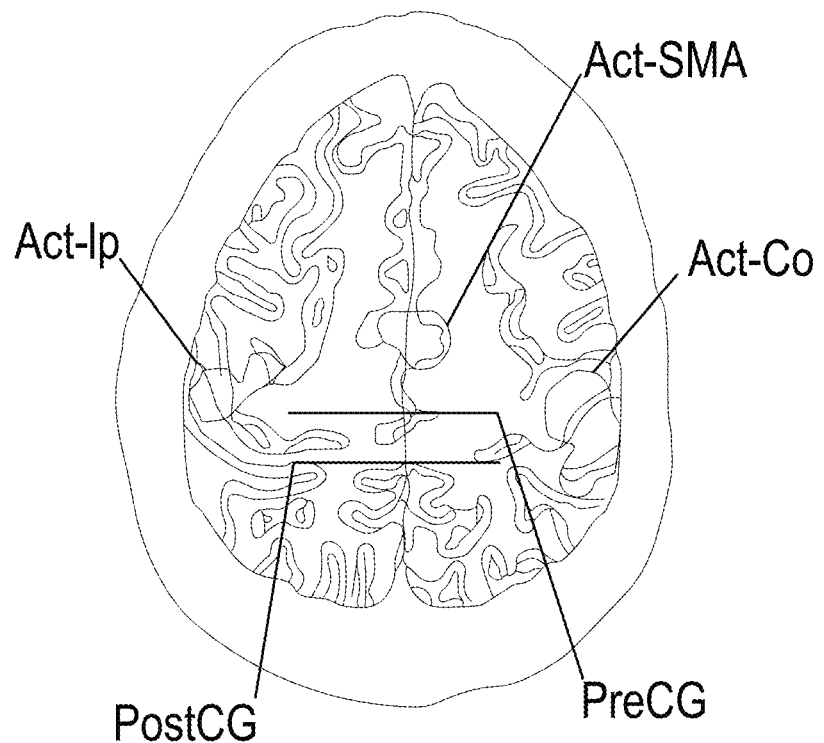
FIG. 3A illustrates an image and annotations, according to an embodiment of the present disclosure.
Figure 3B:
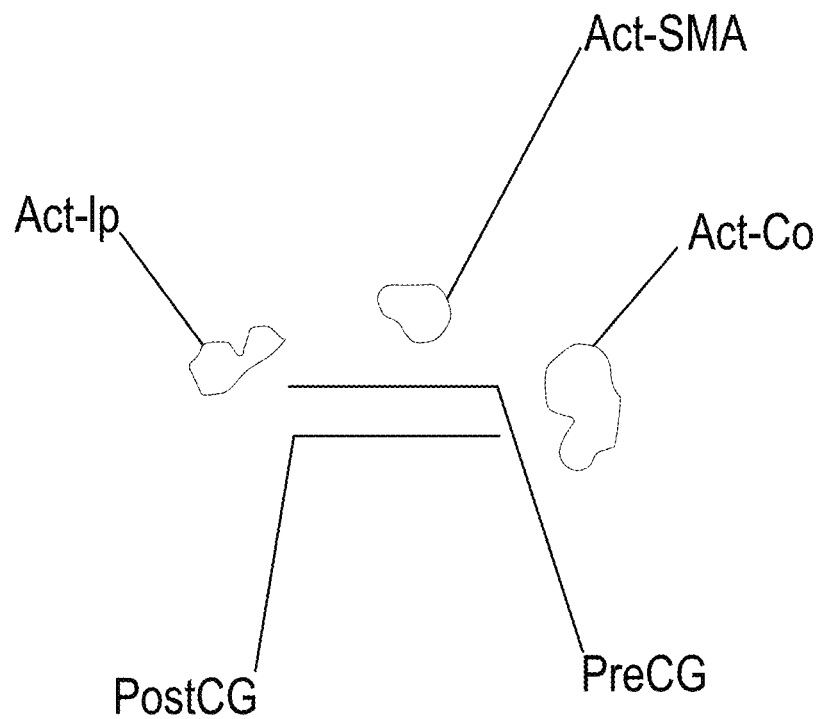
FIG. 3B illustrates non-embedded nature of the annotations in FIG. 3A, according to an embodiment of the present disclosure.

FIGS. 3A and 3B respectively depict a display including an image and a display including the annotations without the image. FIG. 3A illustrates marked regions of interest with respective pointers and labels. As will be appreciated, the annotations may be "overlaid" over the original image and not embedded. Rather, the annotations may be stored in a separate file, which may be linked to the image file. In one specific example, the annotations may be stored in an image independent vector format (i.e., for high-resolution display at all scales). It is noted that the image is unedited and no pixels of the original raster image were modified.

Figure 4:
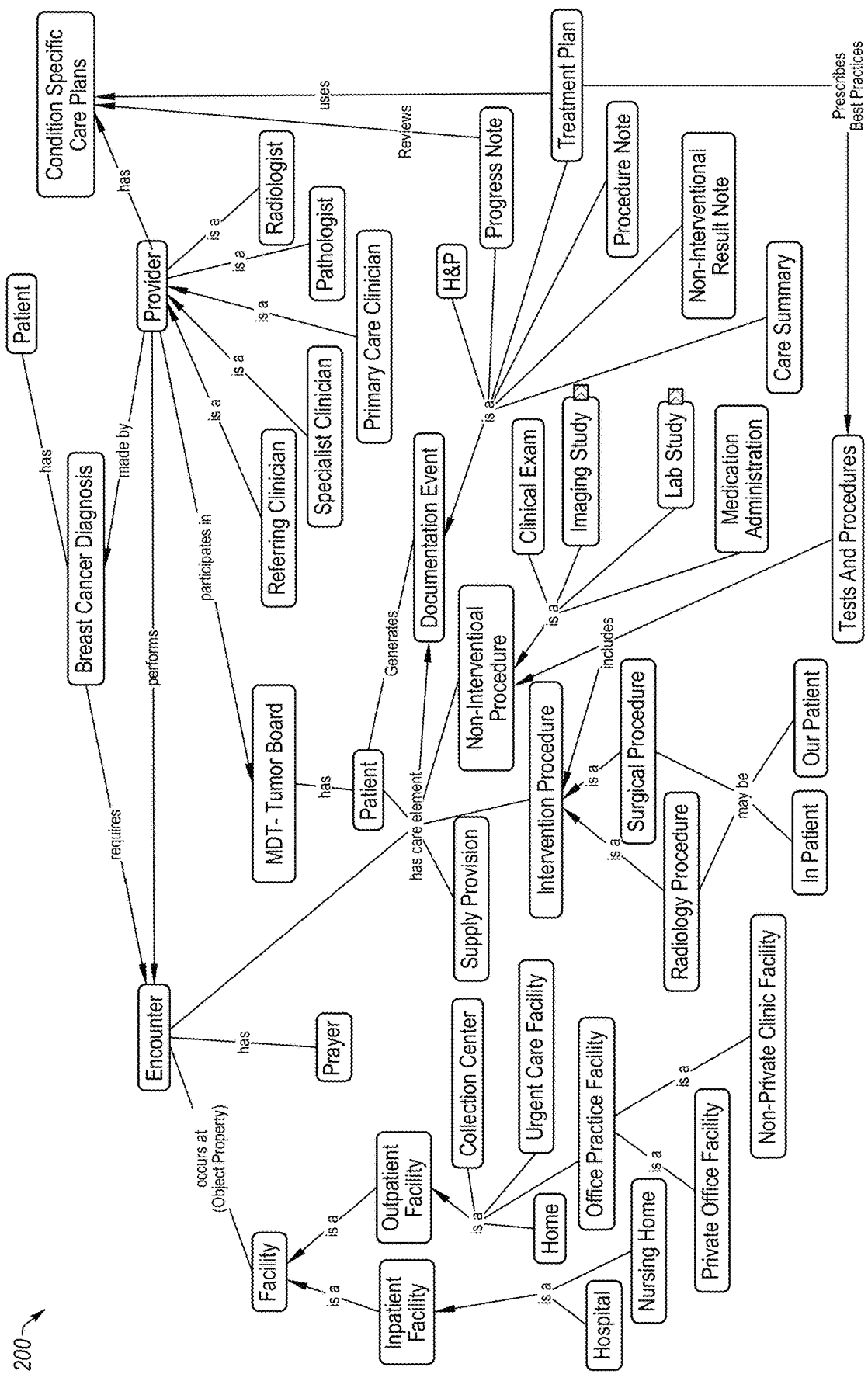
FIG. 4 depicts a map illustrating various stages of a treatment process.

FIG. 4 depicts a cognitive map 200, which illustrates the complex nature and stages of a medical treatment process. As will be understood by a person having ordinary skill in the art, a treatment process may involve various stages and interaction amongst various healthcare personnel from multiple healthcare specialties. Further, the treatment process may include interaction with images, patient information, payers, and a patient.

As will be appreciated, diagnostics and treatment planning may be dependent on bringing members of a care team together for routine review and updates of a treatment plan. For example, in a breast cancer case (e.g., see FIG. 4), data (e.g., imaging and textual inputs) from different specialties (e.g., radiology, surgery, pathology, etc.) perform a critical role in diagnosis. The data may originate from different encounters generated at different times during treatment of a patient. Treatment requires ongoing collaboration between health care professionals (e.g. expert clinicians) of different specialties that form a multi-disciplinary team, which requires access to the patient's data for critical decision making. Ideally, each healthcare professional should review all the patient's data (e.g., within a tumor board or case review) including image data and annotated areas of concern for a particular patient. Further, text records that provide context for the image review such as radiology, surgical and previous pathology reports, remain vital.

A radiology-pathology-oncology breast cancer example is a common scenario. In this example, a female may receive a mammogram that shows a suspicious mass. The mass may be biopsied and sent to pathology where an initial diagnosis begins with screening and identifying suspicious findings from imaging (e.g., via radiology). Further, tissue diagnosis (e.g., via pathology) imaging may occur. Other types of pathology imaging and oncology imaging are routinely accessed and reviewed in multi-disciplinary team evaluation. Moreover, it is becoming more common that additional studies, using biomarkers and sophisticated molecular imaging, may provide the framework for pathologists to contribute significantly to refine treatment pathways that will become routine in personalized therapy. In the breast cancer example (e.g., wherein a patient is diagnosed with breast cancer), images and data critical to the treatment plan may be generated over an extended time period (e.g., 12-18 months).

Record systems, such as, for example only, electronic medical/health record (EMR/EHR) systems, may be designed to manage and depict information. For example, EMR/EHR systems may be configured to manage and depict administrative, logistical and systematic health information for a patient. Current EMR/EHR systems maintain a rigid view of a patient care process and struggle to integrate disparate information sources and heterogeneous provider systems. EMR systems typically do not meet the requirements of a fully engaged multi-disciplinary team process, especially when members of a care team are from disparate organizations. Further, conventional EMR systems may fail to integrate multi-modal imagery, complete annotation, and incorporate multi-disciplinary team contributions to diagnosis, treatment planning, and treatment plan execution. These ridged processes are typically based on a financial model that consistently adds cost to a care process without improving outcomes and/or patient satisfaction.

Further, in the medical field, for example, text-based patient information (e.g., findings, diagnoses and clinical summaries) may reside in separate information systems, which may prohibit timely access by a care team. For example, clinical notes, which may reside in an EMR/EHR and a laboratory information system (LIS), may not be connected to each other or to the imaging systems.

In addition, some conventional systems, which may manage patient records in a chronological or linear manner, are focused on patient records and are not designed to facilitate or support any level of interactivity (e.g., collaboration including specialized tools for visual annotation and real-time communication). These systems may consume images, provided each image is a manageable size, but without the contextual components about the image or set of images leaving the image as an outlier in the system.

Various embodiments of the present disclosure relate to a system (e.g., for clinicians, such as radiologists, pathologists, oncologists, gastroenterologists, and primary care physicians) configured to support diagnosis and treatment planning (e.g., in a virtual tumor board or case review environment). The system may be configured for exchange and management of data including, for example, images and text. It is noted that data (e.g., images and/or text) having a common identifier may be included within a data set. Stated another way, all data within a data set may have a common identifier, such as a patient ID. In one or more embodiments, the system may include a collection of technologies (e.g., modules and/or components) configured to exchange and manage data (e.g., images and/or text) within a data set.

Compared to conventional systems, which may receive images from a single modality (e.g., radiology), various systems, as described herein, are configured to receive, process, and aggregate data (e.g., text and/or images) from different modalities (e.g., radiology, pathology, oncology, dermatology, GI, etc.) into a data set. Thus, a data set may include data from different image modalities and/or medical specialties to support and facilitate evaluation (e.g., multidisciplinary team evaluation), review, and treatment planning (e.g., collaboration). According to various embodiments, relationships among data within a data set may be maintained. For example, data within a data set may be linked via metadata.

A system may be configured to provide a presentation layer (e.g., via a computer screen) or portal that allows for real-time communication with data (e.g., images), supporting the iterative nature of a multi-disciplinary team by allowing specialists to access and review critical information, including clinical summaries from other specialists. Bringing specialists and providers together to evaluate imaging and diagnostic summaries for a case, in stages, in a timely manner, may improve the treatment outcome of the patient. For example, a pathologist may consult with a surgeon and an oncologist. At every step in a treatment process, images may be generated from multiple devices that are unlinked to the patient's health record.

Diagnosis and findings may be important for devising a treatment plan and may require interaction across various specialties (e.g., gastroenterology, radiology, surgery, pathology, oncology, pulmonology, primary care, etc.) to identify the correct treatment planning options. Once treatment is underway, studies may be conducted over a time period (e.g., several months) to determine the effectiveness of treatment and to determine whether changes are necessary. Studies (e.g., imaging studies) may be required to measure the effectiveness of treatment and generate data (e.g., textual findings and images). This data may be reviewed by a care team (e.g., radiology, pathology, and oncology) in formal reviews (e.g., case reviews or tumor boards). Further, additional data (e.g., comments and findings) may be collected regarding the status of treatment and about best practices for refining treatment.

In one specific embodiment, a system may process and aggregate images including annotations (e.g., annotated regions of interest) across image specialties and modalities (e.g., radiology, pathology, surgery and oncology), wherein the annotations (e.g., metadata) may maintain relationships across images one or more images within a data set. Annotated regions of interest (ROI) may maintain a relationship with an original image that may be part of a data set for a given record or case. Annotated ROI may include annotated information to describe a relationship between and across images from a different modality or modality as a group to convey meaning in diagnosis or treatment. The information may be modified (e.g., across clinical imaging modalities) to reflect a change in a record for a given diagnosis and/or treatment plan.

A system may further be configured to group one or more annotations into discrete elements, wherein the one or more annotations may be displayed with one or more images to maintain the data-derived parent-child relationships across different images and textual data from different data modalities. The one or more annotations may provide context to one or more images and/or text in human-readable and machine-consumable formats. As will be appreciated, in various industries (e.g., healthcare, geography, oil and gas, and satellite industries), annotations, and the ability to produce a context specific collection of annotation groups and their metadata layers may be useful for conveying meaningful information for all aspects of digital imaging. It is noted that although various embodiments of the present disclosure are described with reference to healthcare, the present disclosure is not so limited. Rather, other applications, including, for example, geography applications, oil and gas applications, and satellite applications, are contemplated within the scope of the present disclosure. Further, embodiments of the present disclosure are not limited to digital data.

In another specific embodiment, a system may be configured to aggregate, organize and display field of view (FOV) images, wherein the FOV images can be modified to reflect a change in treatment plan or diagnosis. Further, in one embodiment, annotated regions of interest or one or more FOV images may be included in a standardized format (e.g., the Continuity of Care (CCD) reporting format), which may be compliant with the Clinical Document Architecture (CDA). More specifically, in another embodiment, a system may be configured to aggregate and organize specific images (e.g., FOV images) and their annotated regions of interest for inclusion into structured output (e.g., the CCD structured output (i.e., a standard format)) while maintaining relationships with the data (e.g., images and associated textual data) with external systems via metadata layers of the annotations. Further, a system may generate (e.g., output) a combination of annotation regions of interest captured in a FOV from a combination of encounters (e.g., for the purpose of conveying specific information regarding a diagnosis or change in diagnosis).

In one example, a treating oncologist may be able to review with the multi-disciplinary team care team, and with the patient, the annotated regions of interest within different images associated with the diagnosis and generate a CCD integrated output, which can be used for human or system communication such as and electronic medical record (EMR) or electronic health record (EHR).

In one embodiment, the format and type of an output of a system may be a combination of annotation regions of interest captured in a FOV from a combination of encounters (e.g., for the purpose of conveying specific data regarding a diagnosis and/or documentation of relevant changes to a diagnosis). Annotated regions of interest contained in the FOV images may contain relevant data, such as billing codes, lexicons, and vocabularies for external system reference and consumption. The system may index and catalogue all received data for the purpose of search and retrieval across data sets. For example, a number of patients that have received a specific treatment and are in remission may be determined (e.g., via a search).

Moreover, a system may extract specific FOV annotated images for inclusion into a structured output. Also, FOV images may be captured while maintaining annotated regions of interest as a metadata layer, and the FOV annotated images may be provided in a structured output into a CCD structure, which is compliant with the CDA. Furthermore, annotations and other information (e.g., information contained in an annotation, such as in a label and/or caption) may be stored with an image or inside of an image, and may be exported to, for example, the Consolidated-Clinical Document Architecture (C-CDA) standard for structured reporting. FOV images, including annotated regions of interest (e.g., visual, label, caption), may be collected for inclusion into the C-CDA structured output for consumption by an external system, and metadata (e.g., annotations) may include information, which may be processed by the external system. Further, a system may be configured to capture FOV images while maintaining annotated regions of interest (e.g., as a metadata layer) in a manner that is compliant with the Health Information Technology Standards Panel (HITSP) standard, which may allow for external consumption by a separate system.

In one embodiment, annotations (e.g., labels and captions) can be extended to contain discrete pieces of information for clinical documentation, billing and reimbursement, and can be used or reused by an external system to communicate with other external systems. Various embodiments may include tools for visually annotating images with, for example, symbols, labels, captions, billing codes, and vocabularies. These tools may allow for tracking events (e.g., during treatment planning), and, therefore, may allow information to be added as part of a documentation process. Documenting different and iterative cycles and maintaining a collection of information and knowledge generated by a care team becomes part of the encounter-based reporting and potentially billing. As an example, the addition of a semantic ontology may provide flexibility for indexing and decision support extending the value of the information in the collection. Analytics companies can easily integrate with the system and use the collection of data for a variety of uses (e.g., clinical decision support, patient trending, and reimbursement trends).

Various embodiments, as disclosed herein, may be compliant with standard Health Level 7 (HL7) protocols for interfacing to external systems, Integrating the Healthcare Enterprise (IHE) profiles, as well as structured (XML, SVG) messaging for CCD transactions. Moreover, embodiments may be configured to adhere to standard security practices (e.g., maintain Health Insurance Portability and Accountability Act (HIPAA compliance) with user authentication in a role-based access control environment.

Figure 5:
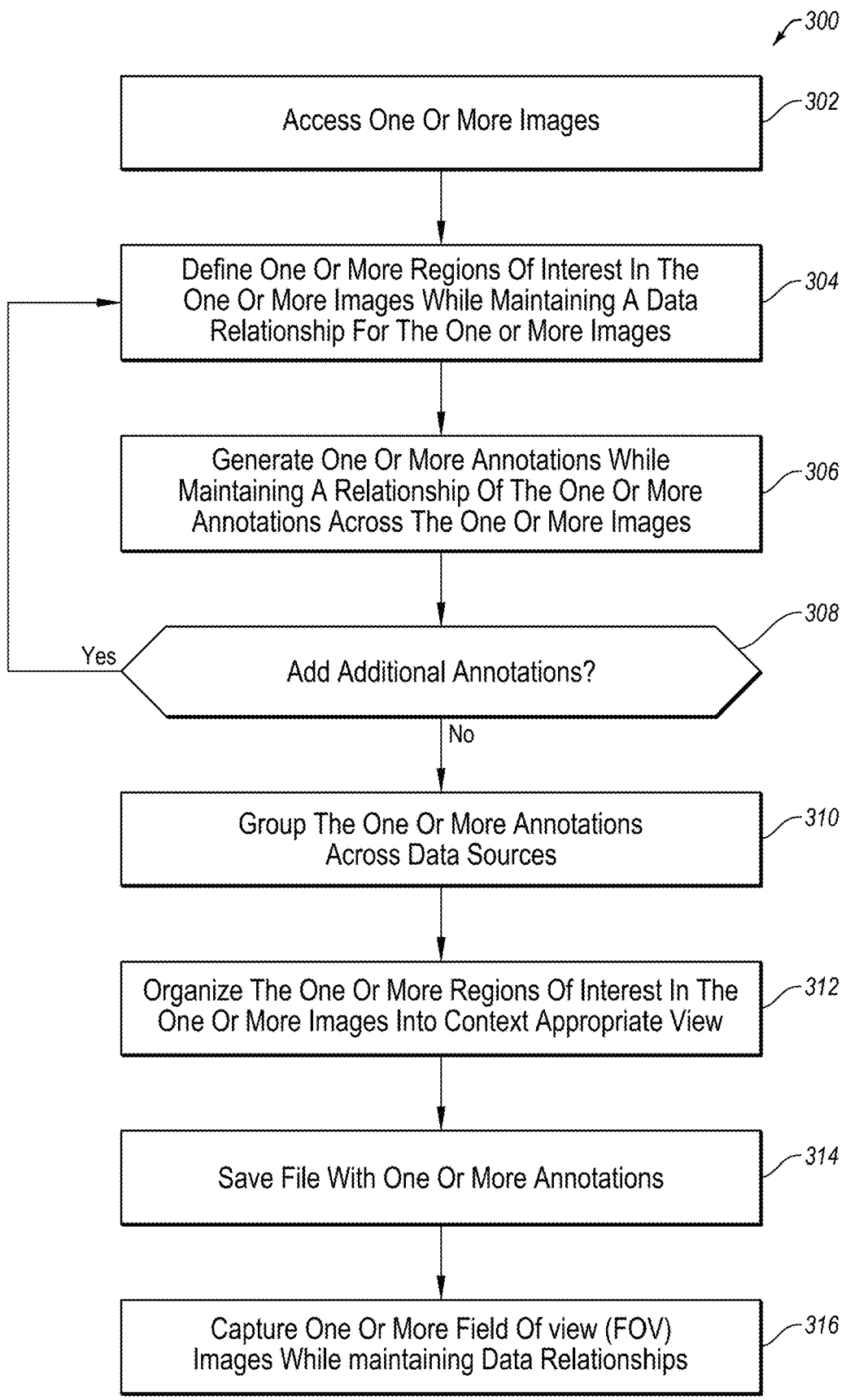
FIG. 5 is a flowchart depicting another method, in accordance with an embodiment of the present disclosure.

FIG. 5 is a flowchart of a method 300, in accordance with an embodiment of the present disclosure. Method 300 includes accessing one or more images (depicted by act 302). Further, method 300 includes defining one or more regions of interest in the one or more images while maintaining relationships for the one or more images (depicted by act 304). More specifically, in one example, a region of interest may be defined in at least one image of a data set, and a relationship of the region of interest may be maintained across two or more images in the data set. Further, method 300 may include generating one or more annotations (e.g., desired symbols, labels and pointers) in the one or more images while maintaining relationships for the one or more images (depicted by act 306). More specifically, for example, at least one annotation for at least one image in a data set may be generated, and a relationship of the annotation may be maintained across two or more images in the data set. Further, method 300 may include determining whether additional annotations should be added (depicted by act 308). It is noted that a person may add annotations to an image, which was already annotated by another person (i.e., "multi-user authoring"). As an example, more than one doctor may annotate the same medical image.

Method 300 may further include grouping the one or more annotations across two or more data sources (e.g., imaging sources) (depicted by act 310). Method 300 further includes organizing the one or more regions of interest in the one or more images (e.g., into context-appropriate views) (depicted by act 312). Context-appropriate viewing (i.e. of an image and related annotations) allows the annotations to be turned on or off for a particular audience. The annotations may be separate from the image, and may be separate from each other, thus, depending on the context, portions of annotations may be viewed in a presentation while other portions remain hidden. Stated another way, a view attribute can turn annotations on/off in a context-appropriate manner. Method 300 may also include saving the file with annotations as vector information linked to the image (depicted by act 314)

Further, method 300 may include capturing FOV images while maintaining data relationships (depicted by act 316). For example, relationships of annotated regions of interest may be maintained across image modalities as a metadata layer.

Figure 6:
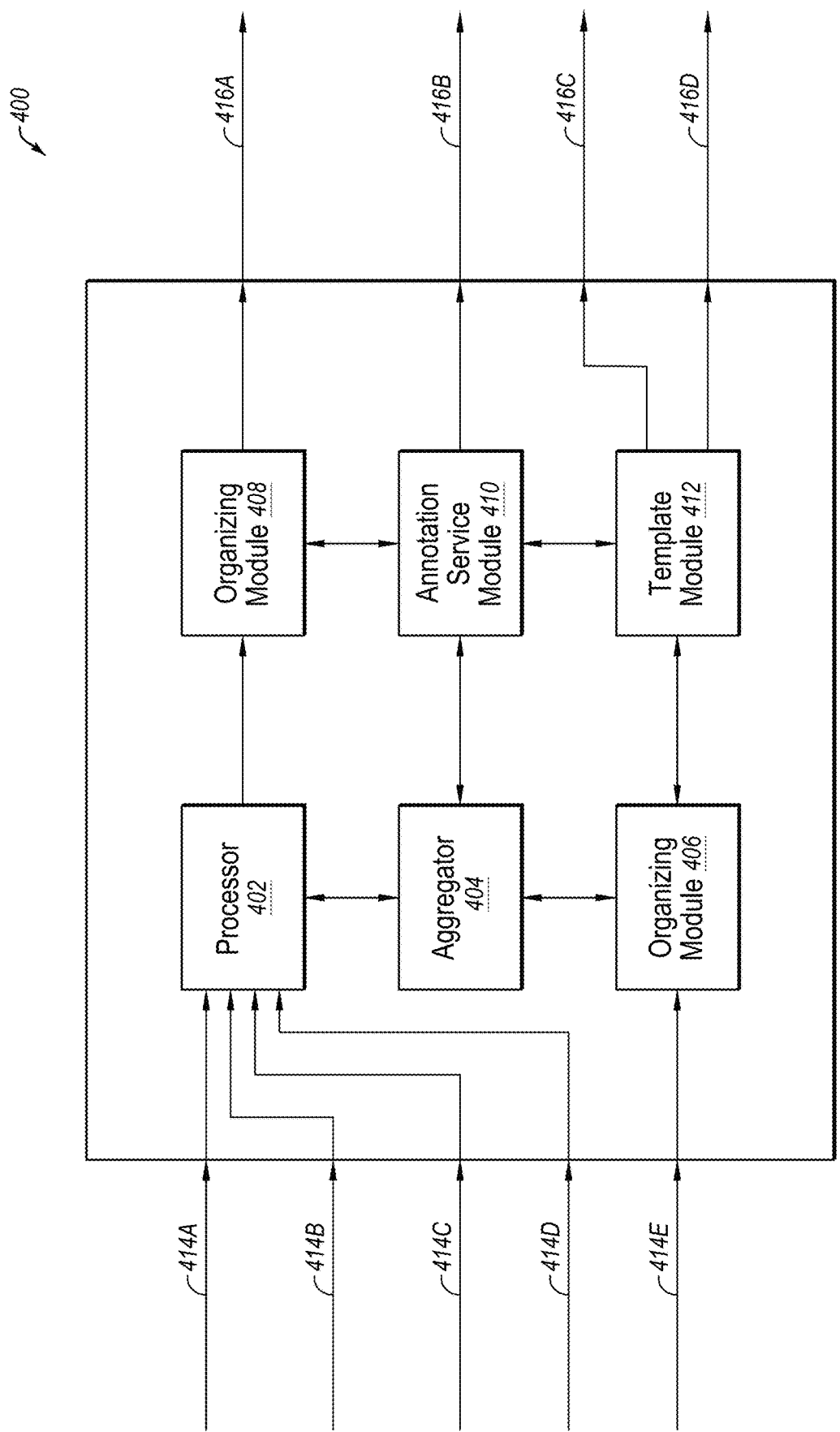
FIG. 6 depicts a system, according to an embodiment of the present disclosure.

FIG. 6 depicts a system 400, according to an embodiment of the present disclosure. System 400 includes a processor 402, an aggregator 404, and organizing module 406, an organizing module 408, an annotation service module 410, and a template module 412. System 400 may be configured to receive data inputs 414, which may comprise images (e.g., from clinical imaging devices), textual information (e.g., from clinical systems), or a combination thereof. Further, system 400 may be configured to process and aggregate data inputs 414, and generate one or more outputs 416, which may comprise machine-readable data (e.g., to be conveyed to an external system), human-readable data (e.g., context appropriate view or presentation) or a combination thereof.

Data inputs 414 may be associated with an identifier (or native metadata), and data inputs 414 having a common identifier may be included within a data set. Stated another way, for example only, all received data associated with a specific patient may have a common identifier and, thus, may be associated with a common data set. Further, data in a data set may originate from, for example, different image modalities and medical specialties.

By way of example, data inputs 414 may comprise data, such as textual data (e.g., structure or unstructured textual data), image data (e.g., structure or unstructured image data), ancillary data (e.g., clinical data, notes, references, etc.), or any combination thereof. Data inputs 414 (e.g., text, images, etc.) of system 400 may be generated via various scenarios. For example, various medical diagnosis and/or treatment processes (e.g., related to breast cancer, lung cancer, skin cancer, colon cancer, etc.) may generate data inputs 414.

Some example scenarios for generating data inputs 414 will now be described. By way of example, diagnosing breast cancer begins with a screening mammogram that generates a set of findings (e.g., text and images) that identify a suspicious mass or lump in the breast tissue. A further imaging study, usually a breast magnetic resonance imaging (MRI) and ultrasound may be required to examine the suspect tissue and determine next steps. Once the suspect mass is identified an ultrasound guided needle core biopsy may collect a piece of tissue from the affected area. The tissue sample may be sent to the pathology lab for a diagnosis. Depending on the diagnosis, the patient either receives a diagnosis of benign and is continually monitored or scheduled for a tumor resection in the event the needle core biopsy is malignant. If the diagnosis is malignant, the patient may be scheduled for a tumor resection and further histological interpretation to determine the type of breast cancer. The pathologist may receive the tissue from the tumor resection and may conduct different tests and studies to determine the type and severity of the breast cancer. Each test and study may generate several images from different devices and text from different systems. The diagnosis of breast cancer may be dependent on the availability of having data (e.g., images and text) from, for example, radiology, surgery, and pathology to determine the best treatment plan options for any given patient. In the case of breast cancer, the diagnosis and findings are important for devising the treatment plan and require a summary and communication across the specialties (e.g., radiology, surgery, pathology) to identify the correct treatment planning options.

Further, lung cancer may be diagnosed upon a patient exhibiting a variety of lung related symptoms. More specifically, for example, a patient, exhibiting a variety of symptoms, such as chronic coughing, chest pain, blood with cough and other symptoms, may be seen by a physician (e.g., primary care physician). The physician may order a specialty set of pulmonary tests combined with other tests such as CT or MRI, as well and needle core or ultrasound guided biopsy to determine the type and severity of lung cancer. The pulmonologist, radiologist and pathologist may work together to review inputs from each specialty to arrive at a diagnosis and continue to review the inputs as the patient undergoes treatment planning. Depending on the type and severity of the cancer, radiation therapy may generate additional images and textual information from other affected parts of the body to measure how the patient is responding to treatment. Images and textual information may be generated from multiple imaging modalities and specialties across the care landscape that are reviewed by all specialty and sub-specialists in the treatment of the patient.

Skin cancer (e.g., melanoma) is an aggressive cancer. When detected, skin cancer may require one or more physicians on a care team to have access to images and/or text (e.g., data inputs 414) that are generated at various stages in the patient's treatment plan. The patient may be seen by, for example, a family physician, or at an emergency room if in late stage melanoma, with symptoms ranging from chest pain, stomach pain, dizziness and fatigue. The patient may undergo imaging, CT, MRI or both, to allow physicians (e.g., radiologists) to view affected areas of the anatomy. The patient may undergo a biopsy where the tissue is seen by another physician (e.g., pathologist) to render a diagnosis. The pathologist and an oncologist may review treatment planning options for a given patient and determine what plan to initiate that provides the most effective treatment and results. The oncologist may use imaging from PET/CT to review how well the patient responds to treatment. All stages in a treatment process may generate data (e.g., multiple images and textual information) inputs that are necessary to measure how well a patient responds, justify treatment, and monitor patients throughout the process.

Diagnosing colon cancer may begin with a colonoscopy, which may generate data (e.g., text and images) that may identify polyps or lumps in the colon, duodenum or stomach. Polyps may be removed and polyp tissue may be sent to the pathology laboratory to determine a diagnosis. Depending on a diagnosis, the patient may either receives a diagnosis of benign and is continually monitored or scheduled for further imaging studies to determine the type and severity if malignant. A further imaging study, usually a colorectal ultrasound, Computed Tomography (CT) and/or MRI may be required to look closely at the suspected area for diagnostic evaluation. A pathologist may receive tissue from the tumor resection and conduct different tests and studies to determine a type and severity of colon cancer. Each test and study may generate several images from different devices and text from different systems (e.g., pathology, oncology, etc.). The diagnosis of colon cancer, like all cancers, may dependent on the availability of having the previous data (e.g., images and text) from, for example, gastroenterology, radiology, surgery, and pathology and oncology to determine the best treatment plan options for any given patient.

Is it noted that the data inputs (e.g., images and textual information) received by system 600 may be unrelated and often is not generated from the same system or from the same institution. For example, the data inputs may originate from geographically separate areas (e.g., geographically isolated clinics, laboratories and hospitals). Further, the data inputs may be generated over long periods of time for a given patient record.

Figure 7A:
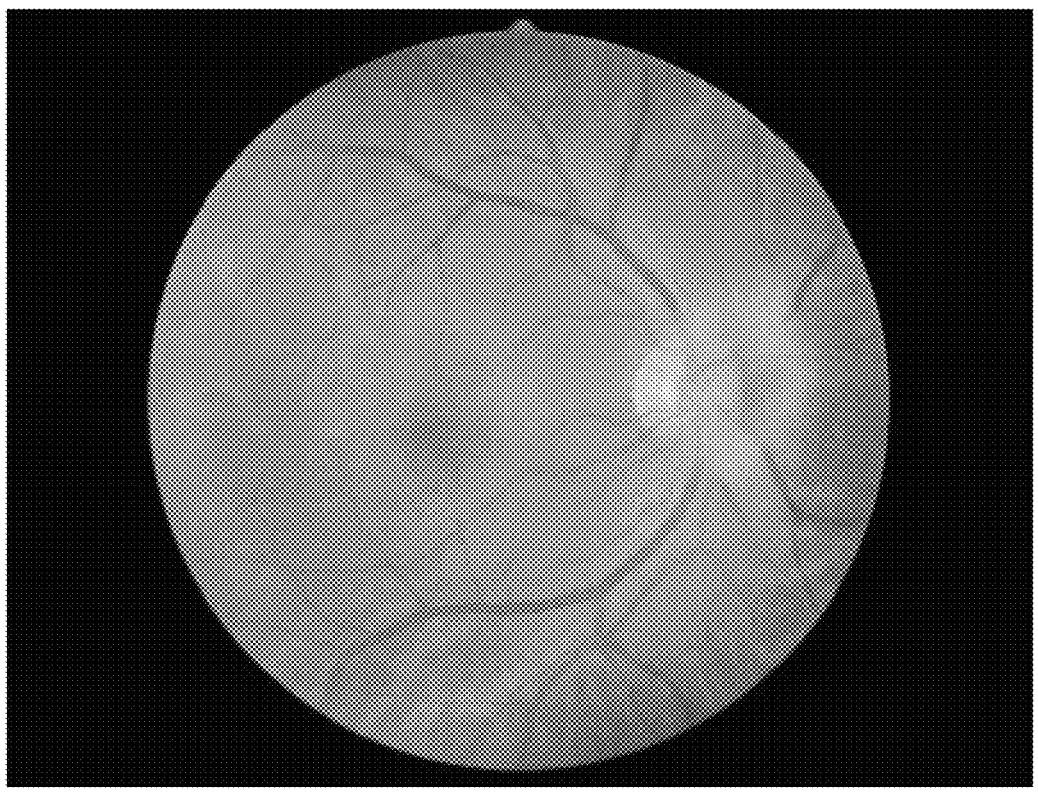
FIGS. 7A-7G depict example input data, in accordance with an embodiment of the present disclosure.
Figure 7B:
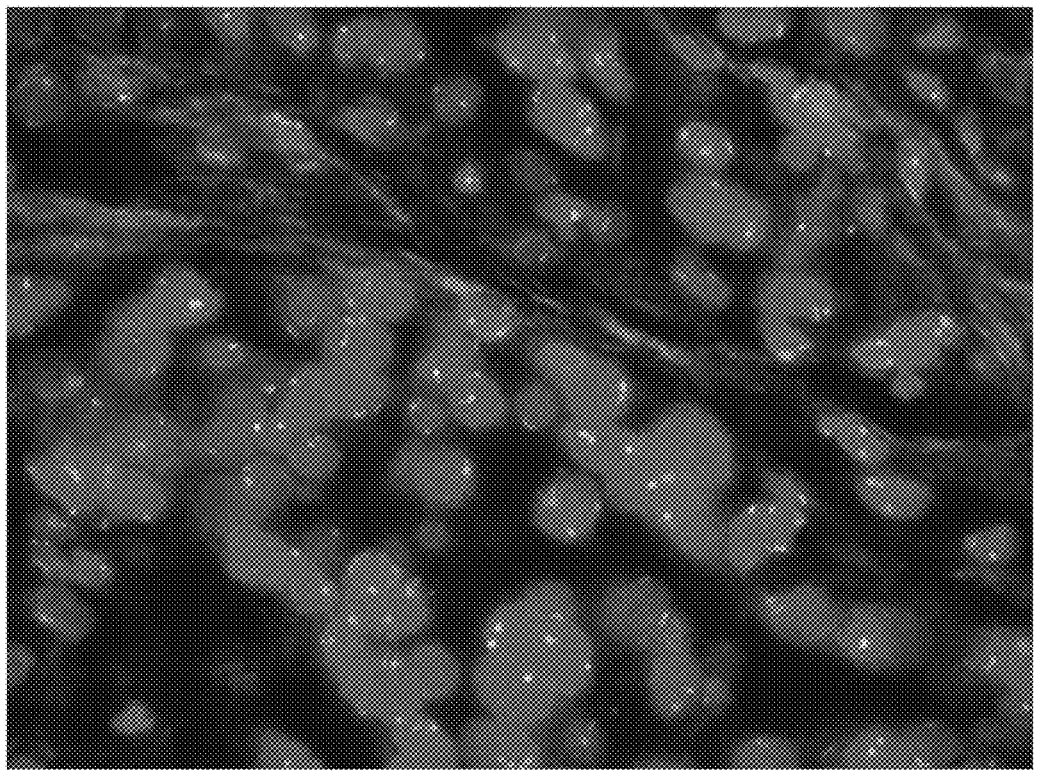
Figure 7C:
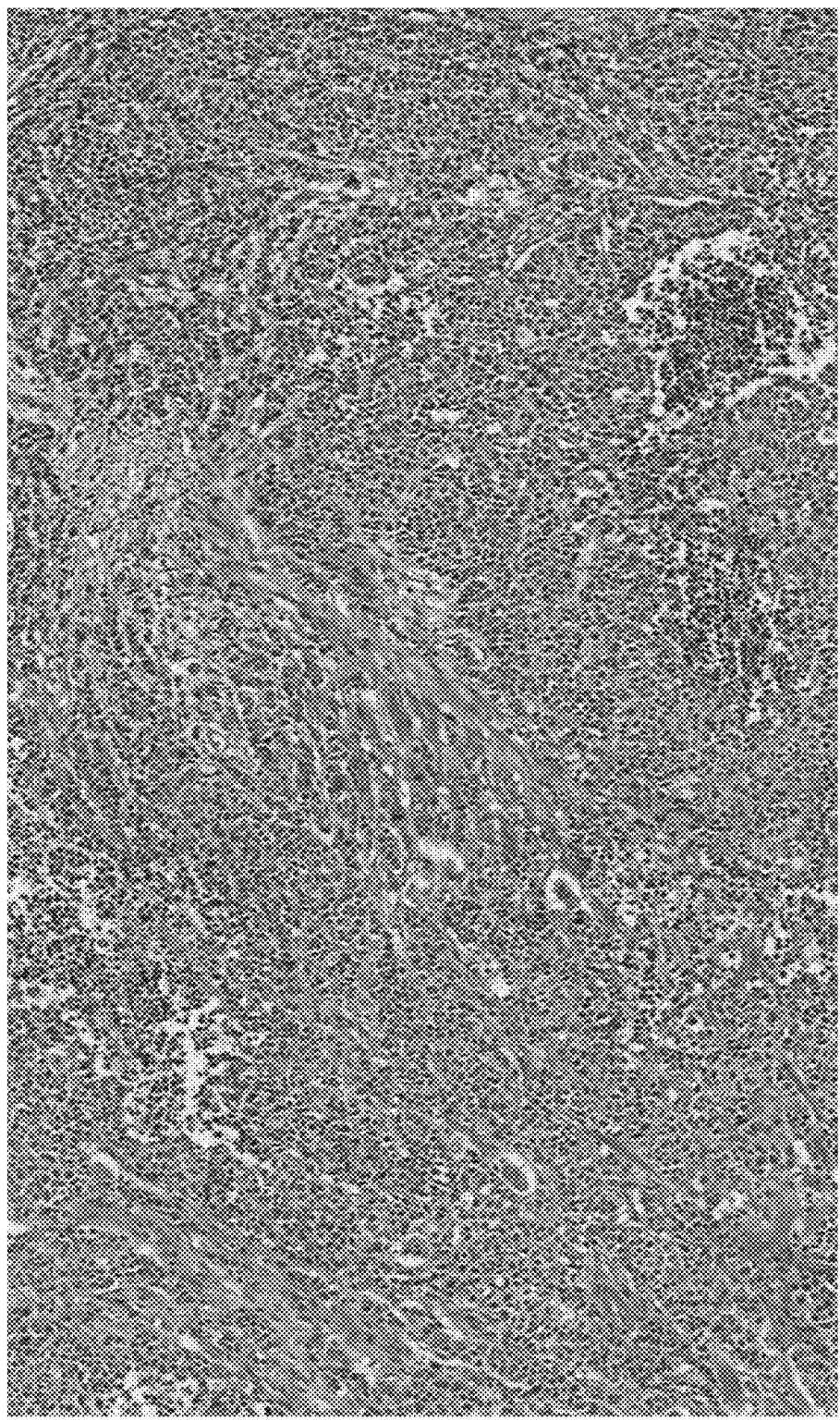
Figure 7D:
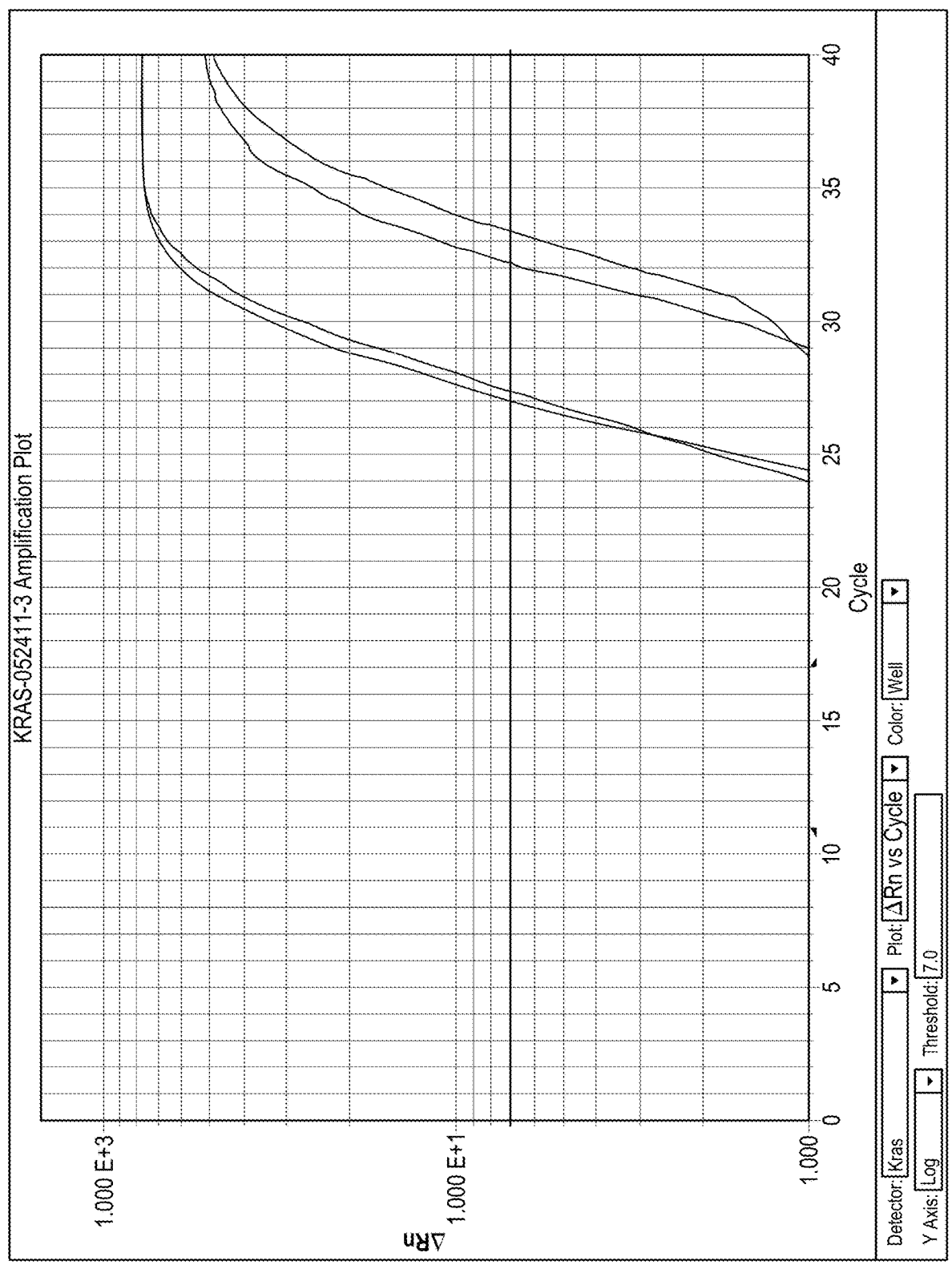
Figure 7E:
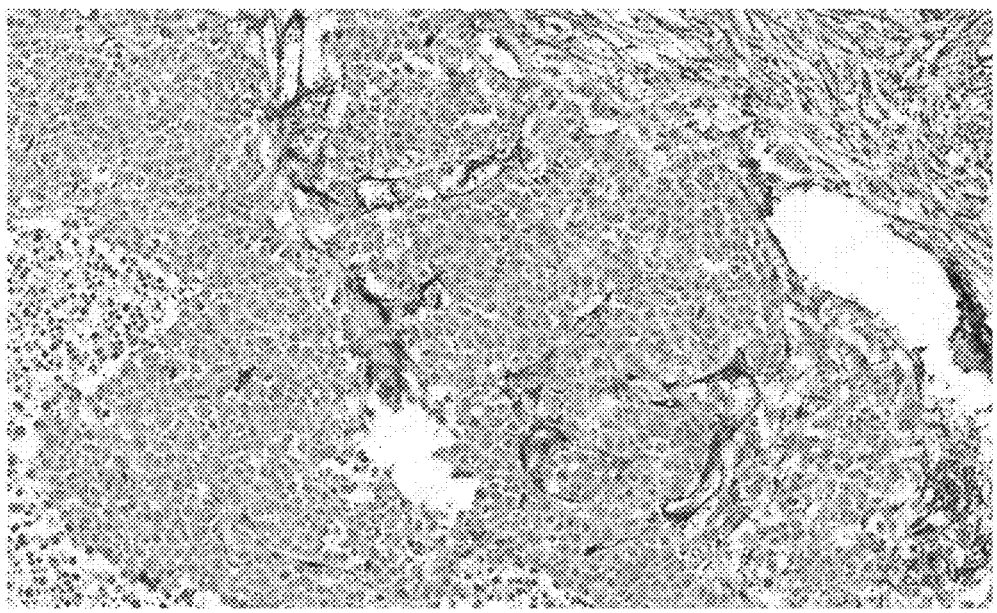
Figure 7F:
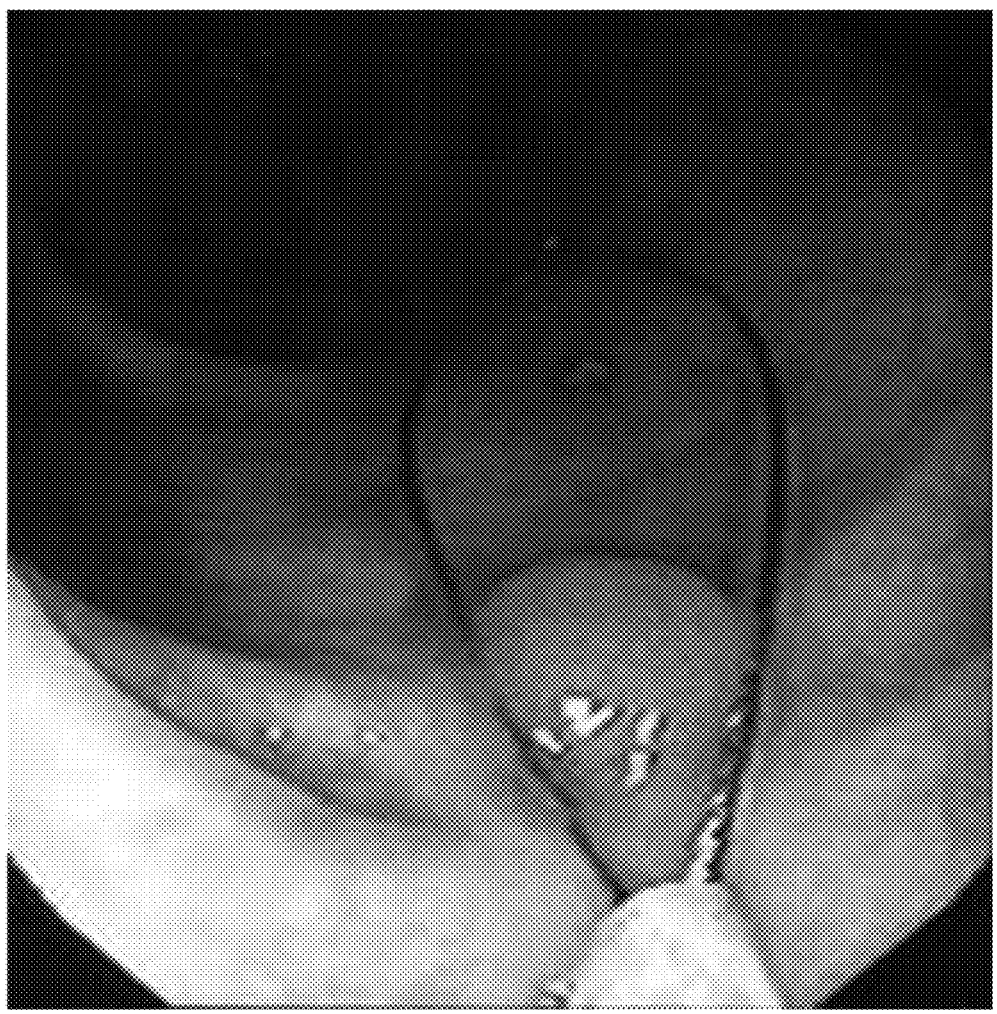
Figure 7G:
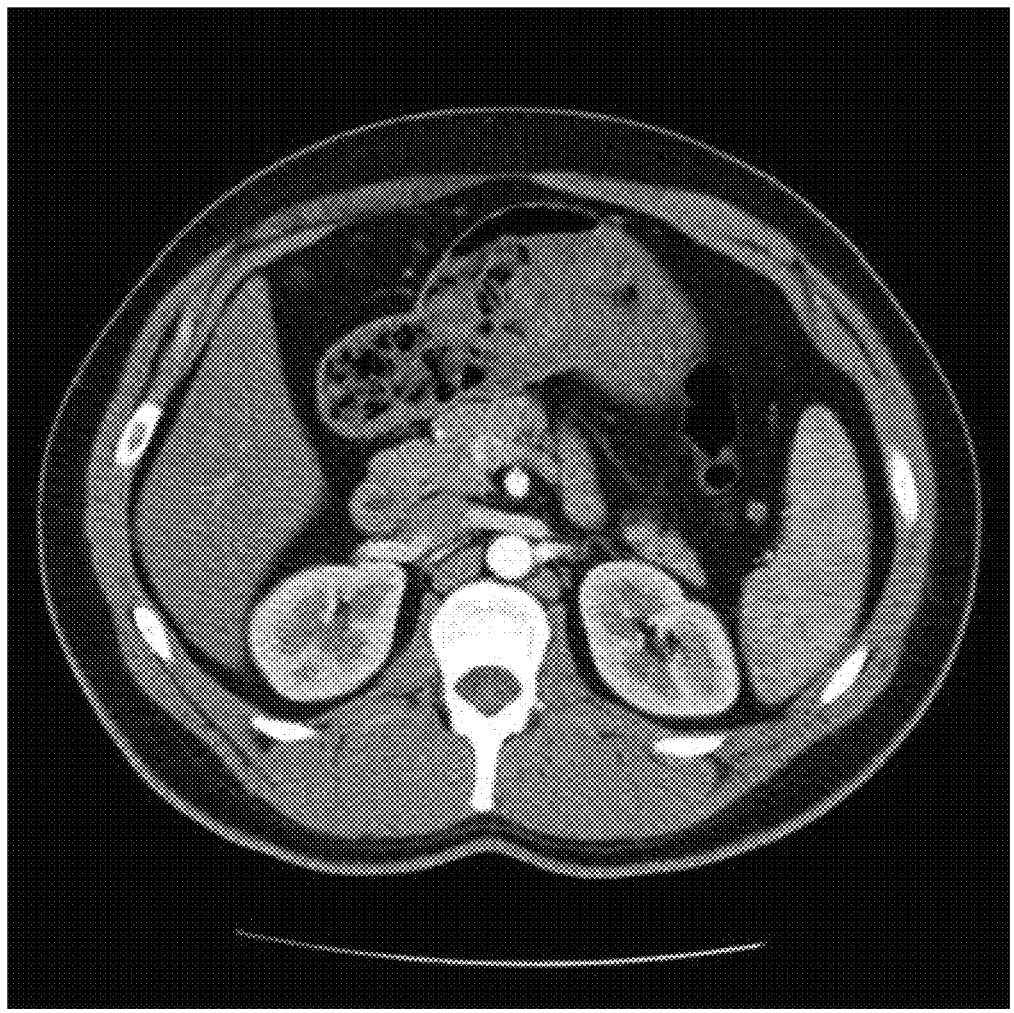

FIGS. 7A-7G depict example inputs (e.g., inputs 414), which may be received by system 400 (see FIG. 6). Specifically, FIG. 7A depicts Ophthalmic image of the retina showing onset of retinitis pigmentosa and FIG. 7B depicts Pathology Fluorescence in Situ Hybridization (FiSH) image showing biomarkers on cancer cells. FIG. 7C illustrates a Pathology Hematoxylin and Eosin stained tissue sample, and FIG. 7D is a Pathology Graph output from Kristen Rat Sarcoma oncogene (KRAS) showing high levels of oncogene protein. FIG. 7E depicts Pathology Beta-type Platelet-derived Growth Factor (PDGFRB) showing prolific cell differentiation in cancer, and FIG. 7F Gastroenterology Colon polyp image during routine colonoscopy. Further, FIG. 7G is a Radiology Transverse Computed Tomography (CT) of the lung and chest.

Referring again to FIG. 6, processor 402 is configured to receive one or more data inputs 414. Further, processor 402 may identify a relationship amongst data inputs (e.g., identifying data inputs that share a common identifier). In one embodiment, processor 402 may receive data inputs and associated metadata at a gross level. Processor 402 may collectively act as a data exchange and accept data inputs (e.g., images and text), which are received (e.g., incrementally) by system 400. In one example, processor 402 may receive data inputs under a source schema and process (e.g., restructure or transform) the data input into a target schema so that the processed data is an accurate representation of the source data (i.e., data inputs 414). Processor 402 may normalize the data inputs to be received by aggregator 404. Further, processor 402 may communicate with aggregator 404 to manage data so that data is maintained together (e.g., in a data set).

Aggregator 404 is configured to receive processed data (e.g., from processor 402) as well as associated metadata. Aggregator 404 may ensure all processed data from processor 402 is managed such that no data is lost. Further, aggregator 404 may manage and assign the processed data to a record ID, which may be maintained by aggregator 404. In one example, aggregator 404 not only manages the gross level metadata but may also assign and/or generate additional metadata across data sets (e.g., as a collection for presentation to a user interface and/or some other output (CCD, report, etc.).

Aggregator 404 may be configured to collect the data sets for, for example, presentation to a user interface. Further, aggregator 404 may call annotation service module 410 to present annotation tools/functionality (arrows, labels, captions, etc.) together with the data set to a user interface. A user interface (e.g., as managed by aggregator 404) may allow for a clinicians, or any other users, to view any or all parts of the data sets received by aggregator 404. Further, the user interface may allow a user to annotate at least a portion of the data within one or more data sets. Users can add descriptions to one or more images that have meaning or describe a specific regions of interest that has a relationship to another region of interest in one or more other images of a data set. Different users may (e.g., via annotation service module 410) add iterative annotations, labels and/or captions that have additional meaning to any combination of the images and text, which may be part of one or more data sets. In one embodiment, annotated information may be managed by aggregator 404.

Aggregator 404 may also aggregate data that may be packaged into increments for a report that is consumed by an external system, a human readable report through template module 412, or annotation service module 410. Aggregator 404 may also be configured to consolidate and manipulate data sets via metadata.

Aggregator 404 may be configured to interact with annotation service module 410 and organizing modules 406 and 408. For example, aggregator 404 may be configured to interact with annotation service module 410 and organizing modules 406 and 408 to maintain and manage the annotations with images and collect and combine the data that is requested by organizing modules 406 and 408.

In one embodiment, aggregator 404 may include a semantic layer that maintains the meanings across the different data inputs (i.e., received by processor 402) as well as meanings that are added through annotation service module 410. For example, a meaning can be derived from an annotation, label, caption, etc. that contains a description of abnormal anatomy added by a physician. This description may be added to data that was consumed from the processor on a prior data (e.g., Jan. 18, 2015). Further, when comparing the data from the prior date (e.g., Jan. 18, 2015) with data that is presented on a subsequent date (e.g., Mar. 8, 2015), a clinician (e.g., a physician), or any number of clinicians, may add annotations, labels, captions, etc. that may contain a different work or phrase but has meaning related to the annotation from the prior date (e.g., Jan. 18, 2015).

Aggregator 404 may manage the meaning (e.g., the information added in iterative cycles, as described the example described above) as an additional layer of metadata across the data set to the record ID for a given patient or instance (e.g., medical, oil and gas, geography, etc.) through the semantic layer. It is noted that a semantic layer may include annotations (e.g., arrows, pointers, circles, and lines), labels, captions and narratives that have meaning for any given user, and which may be linked to a syntax that links the meaning across the data. Aggregator 404 may be configured to maintain relationships between, for example, words, narrative, labels and symbols.

In one embodiment, aggregator 404 may be configured to manage and maintain the relationships of the data inputs (i.e., within a data set) through the use of a semantic ontological framework. The ontological framework (e.g., specific to medicine) may be configured to extract and aggregate information collected from, for example, iterative cycles, as described above. The ontological framework, which may use a common vocabulary in which shared information or knowledge is represented, may also prepare collections of information to allow a user to add a different code (e.g., CPT billing code) to the annotation set. In one example, the annotation set may be submitted to a billing service where the collection of annotated images with their respective regions of interest, labels and captions, along with the billing code, may be collected and queued up for organizer module 406 to send to template module 412 for output.

A semantic-ontological framework may be internal to aggregator 404, and may manage the meaning, which may be part of the collection of larger data sets, and along with other functions of aggregator 404, may be used to communicate with organizing module 406. By way of example, aggregator 404 may generate an output that represents one of the iterative cycles, as described above, with a specific meaning (e.g., the tumor is shrinking) that is documented by, for example, a team of clinical specialists. Further, the output may include a billing code that also includes a quality measure, which may be linked to the data set for that instance at that time. The output may be consumed by organizer module 406 and sent to template module 412. This is one example scenario, and other scenarios, in which aggregator 404 manages a data set, may exist.

Organizing modules 406 and 408 may each be configured to receive inputs (e.g., images and/or text) from both aggregator 404 and annotation service module 410. Organizing modules 406 and 408 may capture inputs with meaningful information contained as, for example, text, annotations, labels and captions for output to template service module 412 or to an external system. Further, organizing modules 406/408 may be configured to maintain relationships across aggregated data and annotations that are added in a temporal sequence. Organizing modules 406 and 408 may be configured to capture a selection of inputs for a given time sequence including FOV information and send that to template module 412 for output to an external system.

Annotation service module 410 may be configured to annotate both images and text, which have been processed and aggregated, and is further configured to maintain relationships across the collection of data. In addition, annotation service module 410 may be configured to annotate regions of interest on a single image, annotate regions of interest across images in a data set (e.g., such that the annotations maintain a specific relationship for a given point in time), store data (e.g., codes and lexicons) for the purpose of documentation, capture FOV that represent an ROI that are sent to the template, or any combination thereof. Annotation service module 410 may provide a user with the ability to interact with images and also maintains relationships through the annotations, labels and captions across the data set.

Template service module 412 is configured to properly format the output from the processed inputs, along with the annotations and relationships with the textual data into a template, which may be in compliance with a standard machine readable output (in the case we are adhering to the Clinical Document Architecture (CDA) Continuity of Care (CCD) standard for external data exchange.

Various embodiments as disclosed herein relate to analyzing and collecting information to develop high-specificity libraries for spatial mapping of cellular/molecular profiles combined with clinical expertise and user-defined markup throughout the multi-disciplinary team and through annotation service module 410. Health care professionals (e.g., clinicians) from multiple specialties may view disparate images from, for example, radiology to complex pathology, in a single view, wherein the cell profiles are linked and mapped across the images for a single case. Further, annotations can identify molecular signals that can be quantitatively mapped across other radiology, pathology, oncology, surgery images, and cell types. Cell class data obtained from cell analysis and mapping may be combined with end-user collaboration metadata in a structured format for use in, for example, cell phenotyping, treatment planning and disease profiling.

Figure 8:
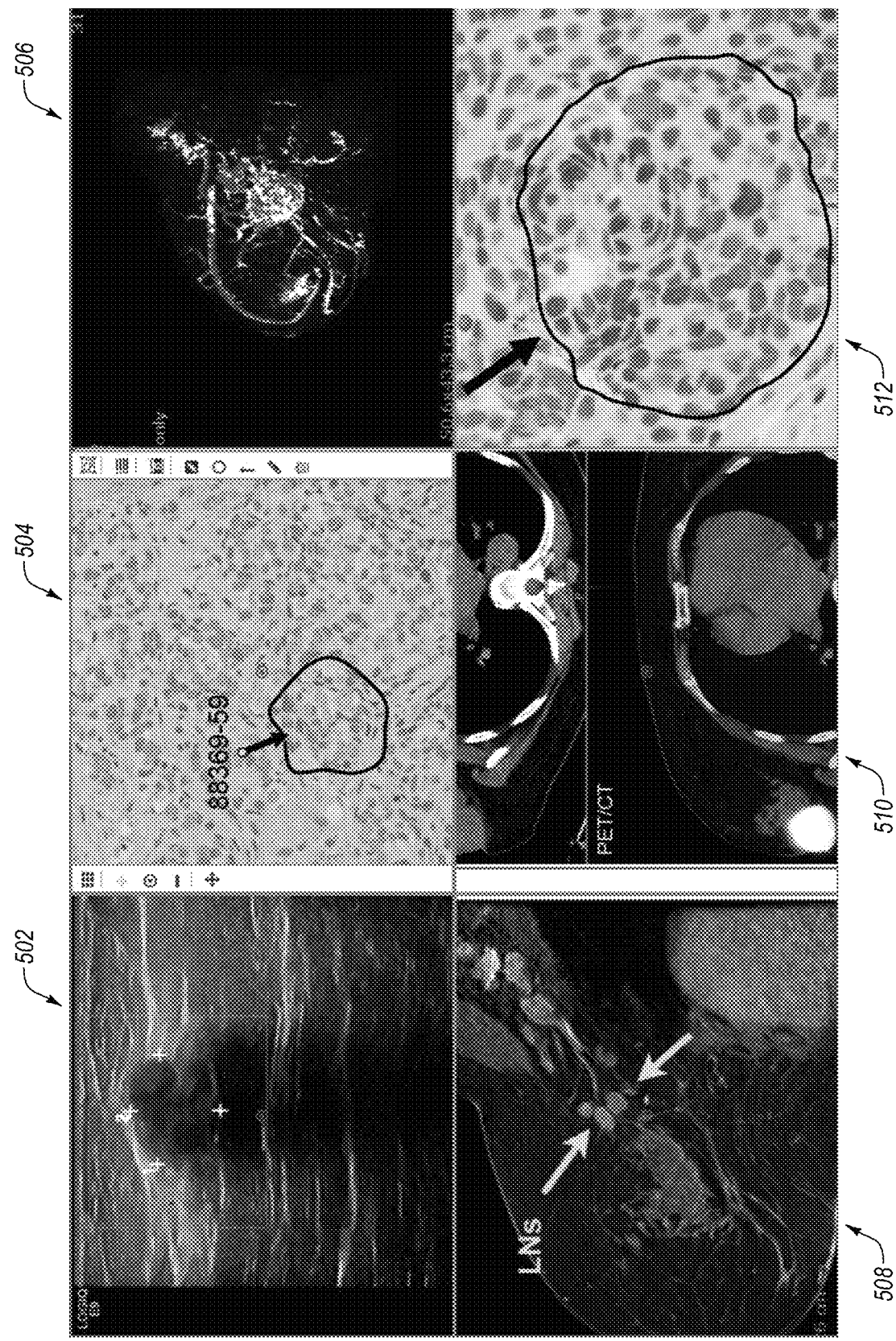
FIG. 8 is a screenshot including a plurality of images, in accordance with an embodiment of the present disclosure.

FIG. 8 is a screenshot (e.g., a presentation to a user interface) depicting a plurality of images, such as an ultrasound image 502, a progesterone receptor (PR) image 504, and a breast magnetic resonance imaging (MRI) image 506. FIG. 8 further includes a human epidermal growth factor receptor (HER2) image 512 depicting tissue biopsies presented together with breast MRI images 506 and 508. FIG. 8 further includes a positron emission tomography and computation tomography (PET/CT) 510, which may be used to determine the anatomic area and expression of genes that have an important role in the development and progression of certain aggressive types of breast cancer. As will be appreciated, FIG. 8 depicts annotations, such as lines, arrows, and codes, that may be maintained across at least some of the images, and may be used for, for example, document treatment planning, billing, and/or patient outcomes.

Figure 9:
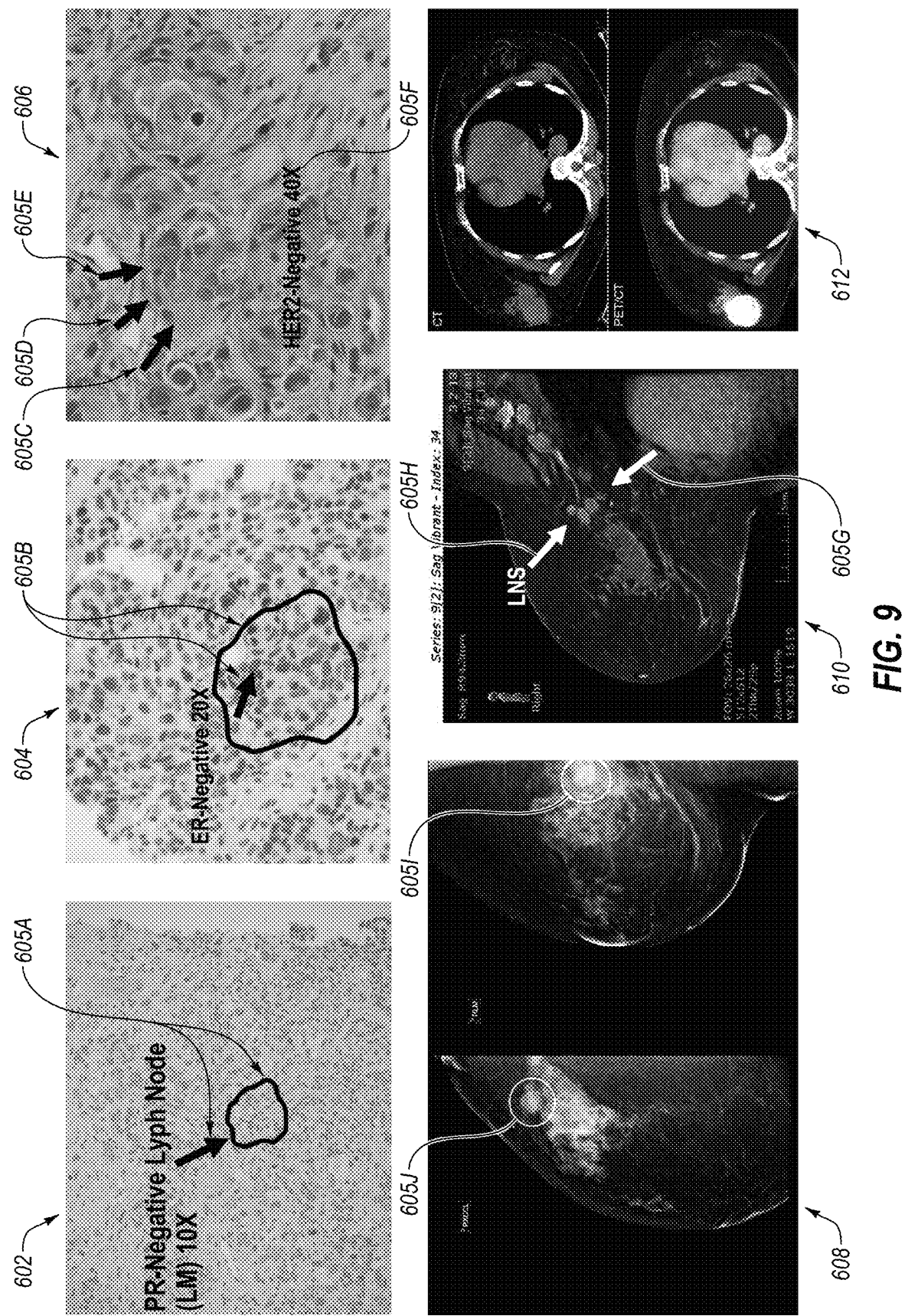
FIG. 9 depicts a plurality of images including annotations, according to an embodiment of the present disclosure.

FIG. 9 depicts aggregated data including breast MRI 608 and 610, and colocalized PET/CT 612 linked to the tissue biopsies and stained ER 602, PR 604, and HER2 606. For example, one or more of the images depicted in FIG. 9 may be used in determining how much overexpressed HER2 protein is present and binding reactions or signals in a patient with triple negative breast carcinoma. The annotated regions of interest 605A and 605B (e.g., a line and an arrow) may link the specific regions of interest for each type of input and may provide the ability to compare, for example, the H&E and HER2 tissue biopsies. As will be appreciated, FIG. 9 depicts annotations 605 (e.g., lines, arrows, text, labels, circles and codes) that may be maintained across at least some of the images, and may be used for, for example, document treatment planning, billing, and/or patient outcomes.

Figure 10:
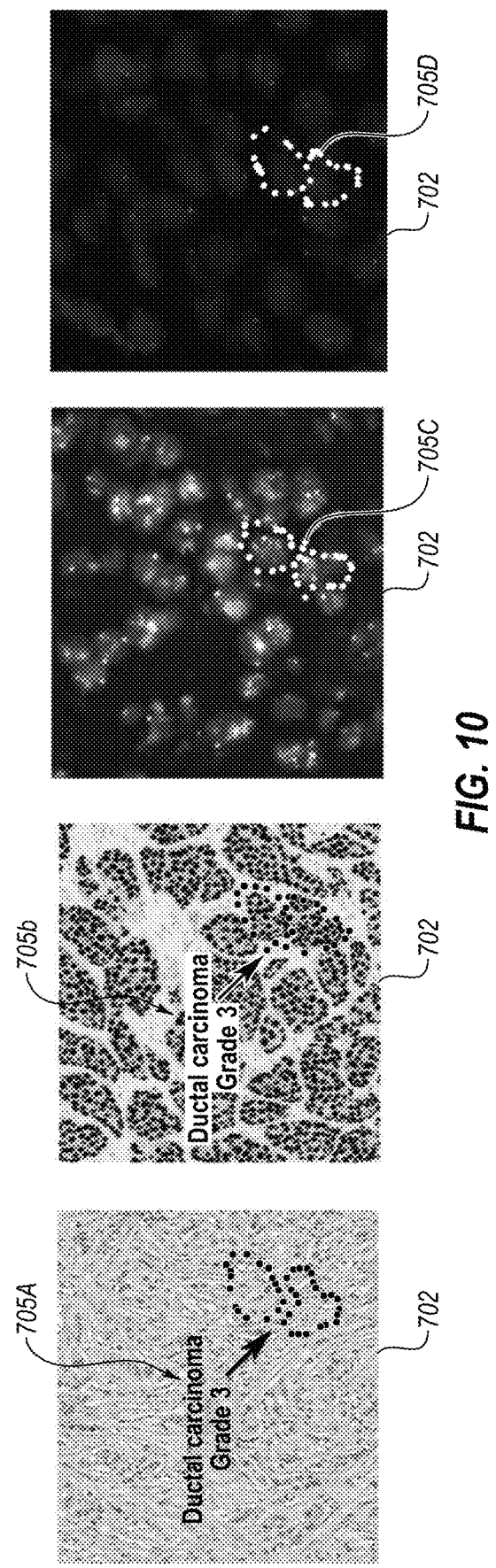
FIG. 10 depicts a plurality of images including annotations, according to an embodiment of the present disclosure.

FIG. 10 depicts a plurality of images 702, 704, 706, and 708 from various modalities (i.e., H&E, Immunohistochemistry and FISH). FIG. 10 further depicts annotations 705A-705D. FIG. 10 illustrates an example of how cells identified in a FISH image may be mapped to H&E and HER2 images of stained tissue sample that have an established relationship for a variety of outputs. As will be appreciated, FIG. 10 depicts annotations 705 (e.g., lines, arrows, text, circles, labels, and codes) that may be maintained across at least some of the images, and may be used for, for example, document treatment planning, billing, and/or patient outcomes.

According to various embodiments, a system (e.g., system 400; see FIG. 6) may enable an end-user to use annotation tools for drawing a region of interest (ROI) on various images, such as image 504 (see FIG. 8) with a Common Procedural Terminology (CPT) code (e.g., 88369), wherein the code may maintain a relationship to a given image and cohort images by system 400. More specifically, codes may be used to link data (e.g., images) within a data set.

FIG. 11 is an example output 800 (e.g., output 416; see FIG. 6), which includes a CCD-A integrated report including annotated regions of interest. More specifically, FIG. 11 depicts an integrated report with annotated regions of interest for a breast cancer case. A CCD-A integrated report may be formatted such that it may render as a readable portable document or may be sent to a patient record in a structured format, which is consistent with the industry CCD-A communication standard. As illustrate, output 800 may include annotations.

Generating a report that encapsulates a collection of data (e.g., diagnostic events, specific FOV from images with annotated regions of interest (e.g., that document the expert findings across the multi-modality care continuum)) may be important for medical treatment (e.g., cancer treatment). According to various embodiments, FOV images may contain metadata that maintains relationships across a data set.

Some embodiments, as disclosed herein, relate generally to aggregating, organizing, and reporting in a standardized format and, more specifically, to collecting field of view images with metadata and aggregating that information with other patient information for generating one or more outputs (e.g., reports). In one embodiment, various systems may be configured for generating an output for reporting to the Centers for Medicare and Medicaid Services (CMS) to meet the requirements for the Physician Quality Reporting System.

As will be appreciated by a person having ordinary skill in the art, CMS have several quality initiatives that provide information on the quality of care across different settings, including hospitals, skilled nursing facilities, home health agencies, and dialysis facilities for end-stage renal disease. These quality initiatives may aim to empower providers and consumers with information that would support the overall delivery and coordination of care, and ultimately may support new payment systems that rewards physicians for providing improved quality care, rather than simply paying based on the volume of services.

Under the Tax Relief and Health Care Act of 2006 (TRHCA), CMS implemented the Physician Quality Reporting Initiative (PQRI) (now called Physician Quality Reporting System (PQRS)) with a bonus payment of 1.5 percent for successful participation based on the estimated total allowed charges for all cover services during the reporting period. Physicians and non-physician providers who participate in the program transmit data to CMS regarding the quality measures reported on in caring for their Medicare patients. Under the Medicare Improvement for Patients and Providers Act of 2008 (MIPPA), the PQRS program was made permanent. MIPPA also requires CMS to post on a website the names of eligible professionals and group practices who have satisfactorily reported under the PQRS. This information, along with additional measure performance information, is now posted on the Medicare Physician Compare website.

Several PQRS program changes were included in health care reform legislation enacted in 2010. The Affordable Care Act (ACA) requires the implementation of timely feedback and the establishment of an informal appeals process by year 2011. The ACA also calls for PQRS payment penalties starting in 2015. CMS finalized, in its 2012 Medicare Physician Fee Schedule rule, that 2015 program penalties are based on 2013 performance. Therefore, physicians who elect not to participate or are found unsuccessful during the 2013 program year, will receive a 1.5 percent payment penalty, and 2 percent thereafter. In the 2014 Medicare Physician Fee Schedule Rule, CMS finalized its proposal to base 2016 PQRS penalties off of 2014 reporting. Therefore, physicians who did not participate in PQRS in 2014 will receive a 2 percent penalty in 2016. The year 2014 was the last year a physician could receive an additional incentive for participating in the PQRS Maintenance of Certification (MOC) program or receive an incentive for participating in PQRS. In the 2015 Medicare Physician Fee Schedule Rule, CMS finalized its proposal to base 2017 PQRS penalties off of 2015 reporting.

PQRS is a reporting program that uses a combination of incentive payments and negative payment adjustments to promote reporting of quality information by eligible professionals (EPs). The PQRS program provides an incentive payment to practices with EPs (identified on claims by their individual National Provider Identifier (NPI) and Tax Identification Number (TIN)). EPs satisfactorily report data on quality measures for covered Physician Fee Schedule (PFS) services furnished to Medicare Part B Fee-for-Service (FFS) beneficiaries (including Railroad Retirement Board and Medicare Secondary Payer).

Beginning in 2015, the PQRS program also applies a negative payment adjustment to EPs who do not satisfactorily report data on quality measures for covered professional services. The Medicare Physician Compare website serves as the primary and authoritative source for all publicly available information and CMS-supported educational and implementation support materials for PQRS.

A qualified clinical data registry (QCDR) is a new reporting mechanism available for the PQRS beginning in 2014. A QCDR will complete the collection and submission of PQRS quality measures data on behalf of EPs. For 2014, a QCDR is a CMS-approved entity that collects medical and/or clinical data for the purpose of patient and disease tracking to foster improvement in the quality of care provided to patients. EPs who satisfactorily participate in PQRS through a QCDR may earn the 2014 incentive payment (0.5%) and avoid the 2016 payment adjustment (2.0%). To be considered a QCDR for purposes of PQRS, an entity must self-nominate and successfully complete a qualification process.

Various embodiments of the present disclosure relate to collecting data (e.g., FOV images with metadata) and aggregating the data with other patient information for reporting to CMS to meet the requirements for the QCDR that is PQRS. Various embodiments may be configured to collect and report on the image-based Quality Measures (QM) that are identified in the PQRS. Conventional solutions only address text-based QM and fail to address the specialty specific QMs in pathology or cancer diagnostics. In contrast, various embodiments disclosed herein provide for aggregation of data for reporting across unformatted systems that function as a definitive source of treatment plans and treatment summaries. Further, various embodiments may provide both textual and image based summaries (e.g., a CCD-A integrated report). As will be understood, QMs are designed to address and document effective clinical care, care coordination and cost reduction and efficiencies.

FIG. 12 includes a table 900 titled "Focus on Dermatopathology: Skin Cancer Quality System." As will be understood by a person having ordinary skill in the art, table 900 may represent a process of a quality system for dermatopathology specifically, melanoma. The QMs (in addition to the Federal core measures) are PQRS 137, 138, 194 and 224. Each of these QMs depend on capturing a series of encounters and documenting them through an accounting system that also provides a means for communication with the primary care or dermatologist in the particular case. To specify the methodology, embodiments of the present disclosure are extended to collect various encounters (regardless of image or multi-disciplinary team), consume information from outbound health level 7 (HL7) feed as an encounter, and index the collection of data linked to a master patient index (MPI). One deficiency of conventional systems and methods is revenue accounting to triangulate the information for accounting purposes and reporting.

An example of a single PQRS reporting will now be described. Hospital administrators and physicians may be able to perform certain national quality metrics through via one or more of the embodiments of the present disclosure. The first quality metric that may be available to all participating sites may be PQRS measure #147, which is titled "Nuclear Medicine: Correlation with Existing Imaging Studies for All Patients Undergoing Bone Scintigraphy" and includes the following description: Percentage of final reports for all patients, regardless of age, undergoing bone scintigraphy that include physician documentation of correlation with existing relevant imaging studies (e.g., x-ray, MRI, CT, etc.) that were performed.

Various embodiments may provide the necessary support for clinicians at hospitals and in other health care settings to better coordinate care for patients beginning with radiographic digital imaging in a manner that will benefit patient care by objective measurements.

Of the approximate 129 PQRS measures currently in use, there are 24 required radiological information standards to be shared between hospitals and physicians (see e.g., https://www.cms.gov/PQRS/), Public Law 109-432; Public Law 110-275). Radiological reports that must be shared include Computer Tomography ("CT"), Positron Emission Tomography ("PET"), Magnetic Resonance Imaging ("MRI"), Mammography, Plain Films (e.g., chest x-ray), and Bone Scintigraphy (i.e. bone scan) for a variety of specific purposes that include various cancers (9 measures), COPD (2 measures), Community Acquired Pneumonia (4 measures), Arthritis (2 measures), Osteopenia (4 measures), and Stroke (2 measures). The only general radiology PQRS measure is for a registry of all radiology reports, both past and future, to be correlated to Bone Scintigraphy (bone scan) PQRS measure #147. It is widely accepted that many, if not all radiology imaging services, have a need to request and share bone scans from a variety of other imaging centers. Bone scans are routine procedures from evaluation for fractures to a series of scans coordinated with other imaging such as MRI, PET, CT, and plain films to rule out metastases.

Hospital and physician administrators generally lack the technology and methods to comply with PQRS Measure #147 in a scalable manner. Various embodiments, as disclosed herein, address physician compliance in addition to image sharing that provides shared savings to the physician and credit for the participating site for meeting one PQRS measure. By supporting the national quality goal as defined by Centers for Medicare and Medicaid ("CMS"), embodiments of the present disclosure may assist those health system administrators struggling to make their health system IT infrastructure compliant to emerging and existent regulatory requirements. Various embodiments may also allow for expansion into other quality projects involving radiology, especially in orthopedics, rheumatology, and cancer related conditions.

It is noted that table 900, and more specifically, QM codes, may be associated with annotations (e.g., CPT codes) used with images. For example, with reference to FIGS. 6 and 12, the same principles described above for aggregator 404 may be applied. In this case, a melanoma example may be used to produce an output that is a machine readable format, such as table 900 of FIG. 12. Data inputs (e.g., images and/or text), one or more processes, aggregation, semantics, ontologies and annotation may produce an output.

If the same principles are applied, collection and review of data inputs (e.g., images and/or text) may be desirable. In one specific example, one or more images may be of a skin screening (e.g., to look at moles and determine is a mole looks suspicious). If the mole is suspicious, the patient may be refereed to surgery (e.g., for excision of the lesion and so forth).

In one example, one or more diagnostic codes (e.g., classification of disease ICD-10 code) and/or one or more CPT codes may be linked to a quality measure code (e.g., PQRS 26, 27 138 and 194 and QOPI 1; see FIG. 12). All of the above codes that comprise of billing for reimbursement and establishing quality are documented by all that takes place in aggregator 404 that is managed with a clinical diagnosis, which may include clinical information.

According to one example, an output 416 of system 400 (see FIG. 6) may comprise table 900. In this example, system 400 may process annotated inputs (e.g., images and text) into a format defined by template module 412 for consumption into an external system (EMR, LIS) or to an external entity (e.g., Centers for Medicaid). The format may include the annotated FOV images that may include codes maintained by annotation service module 410.

Figure 13:
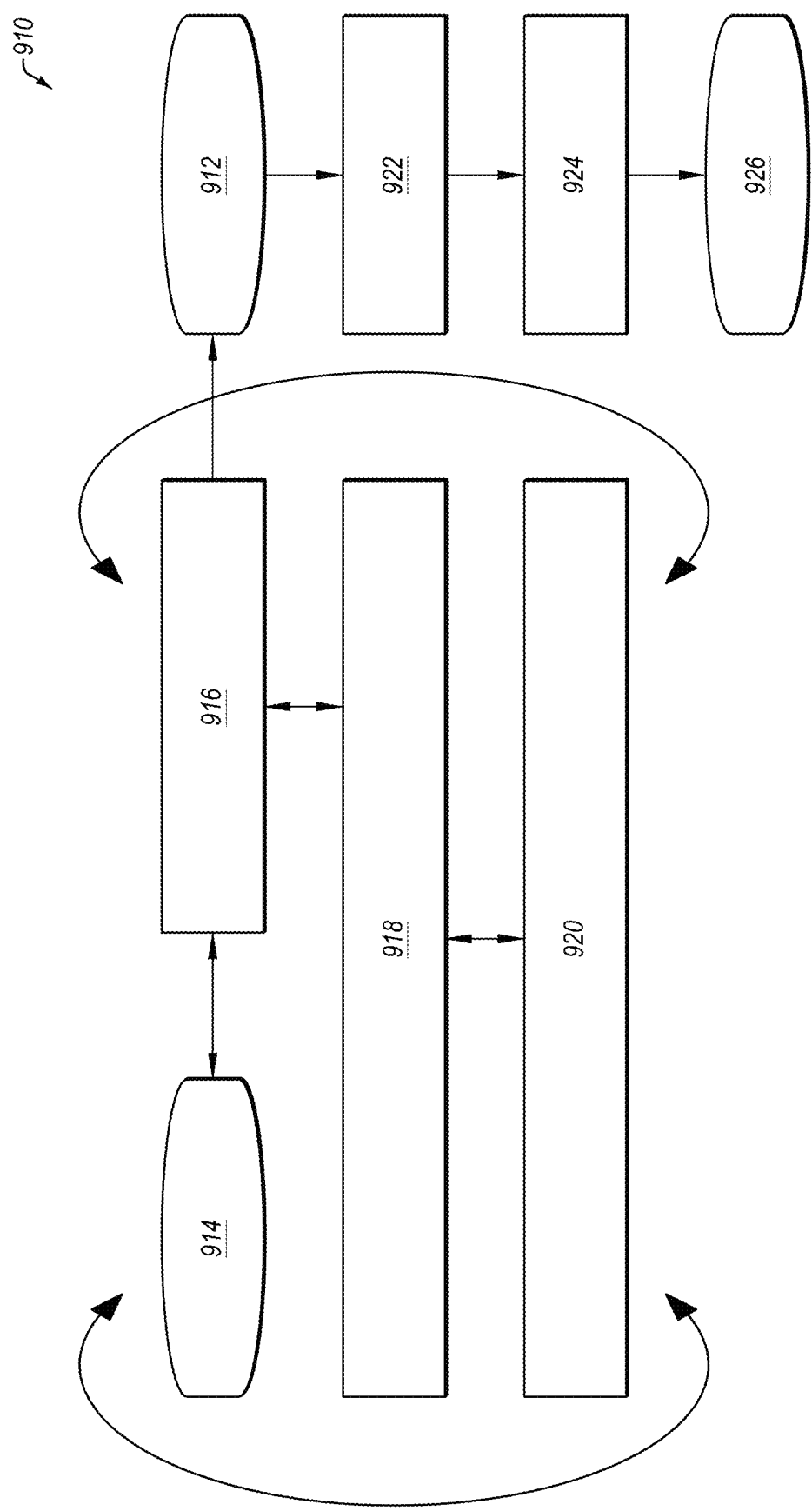
FIG. 13 depicts a system, in accordance with an embodiment of the present disclosure.

FIG. 13 illustrates a system 910 including a platform 912, in accordance with an embodiment of the present disclosure. In addition to platform 912, which may comprise a QM platform, system 910 includes a system (e.g., a laboratory information system or external system) 914, a Health Economics Optimization and Revenue Performance Management module (e.g., an XIFIN® Health Economics Optimization and Revenue Performance Management module) 916, an image-based QM library 918, a care team collaboration platform 920, an external system (e.g., an electronic health records system, an electronic medical records system, or a laboratory information system) 912, and CMS 924. System 900 may also include another platform 926, which may also comprise a QM platform.

The output of the reporting system 900 may comprise the following formats: 1) structured to be machine readable by larger enterprise systems (EMR) and consumed by CMS and 2) rendered into a common format for human consumption. The system organization intelligence structure process may determine the necessary output for many destinations. Input into the system is collected from external billing, revenue cycle and patient record systems, aggregated and organized into a structure type based on parameters passed to system 900. It is noted that module 916, library 918, and/or platform 920 may comprise system 400, as illustrated in FIG. 6

Figure 14:
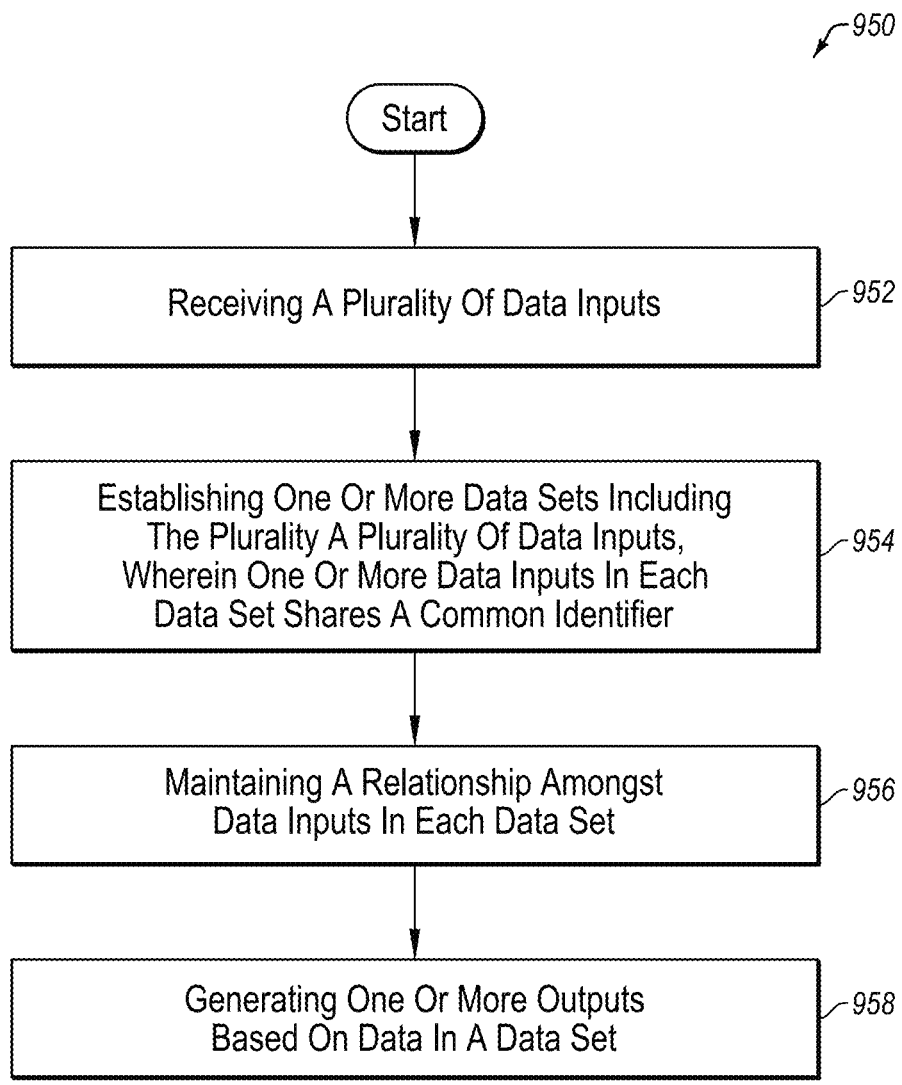
FIG. 14 is a flowchart depicting another method, according to an embodiment of the present disclosure.

FIG. 14 is a flowchart of a method 950, according to an embodiment of the present disclosure. Method 950 includes receiving a plurality of data inputs (act 952). Method 950 further includes establishing one or more data sets including the plurality a plurality of data inputs, wherein one or more data inputs in each data set shares a common identifier (act 954). In addition, method 950 includes maintaining a relationship amongst data inputs in each data set (act 956). Moreover, method 950 includes generating one or more outputs based on data in a data set (act 958).

Figure 15:
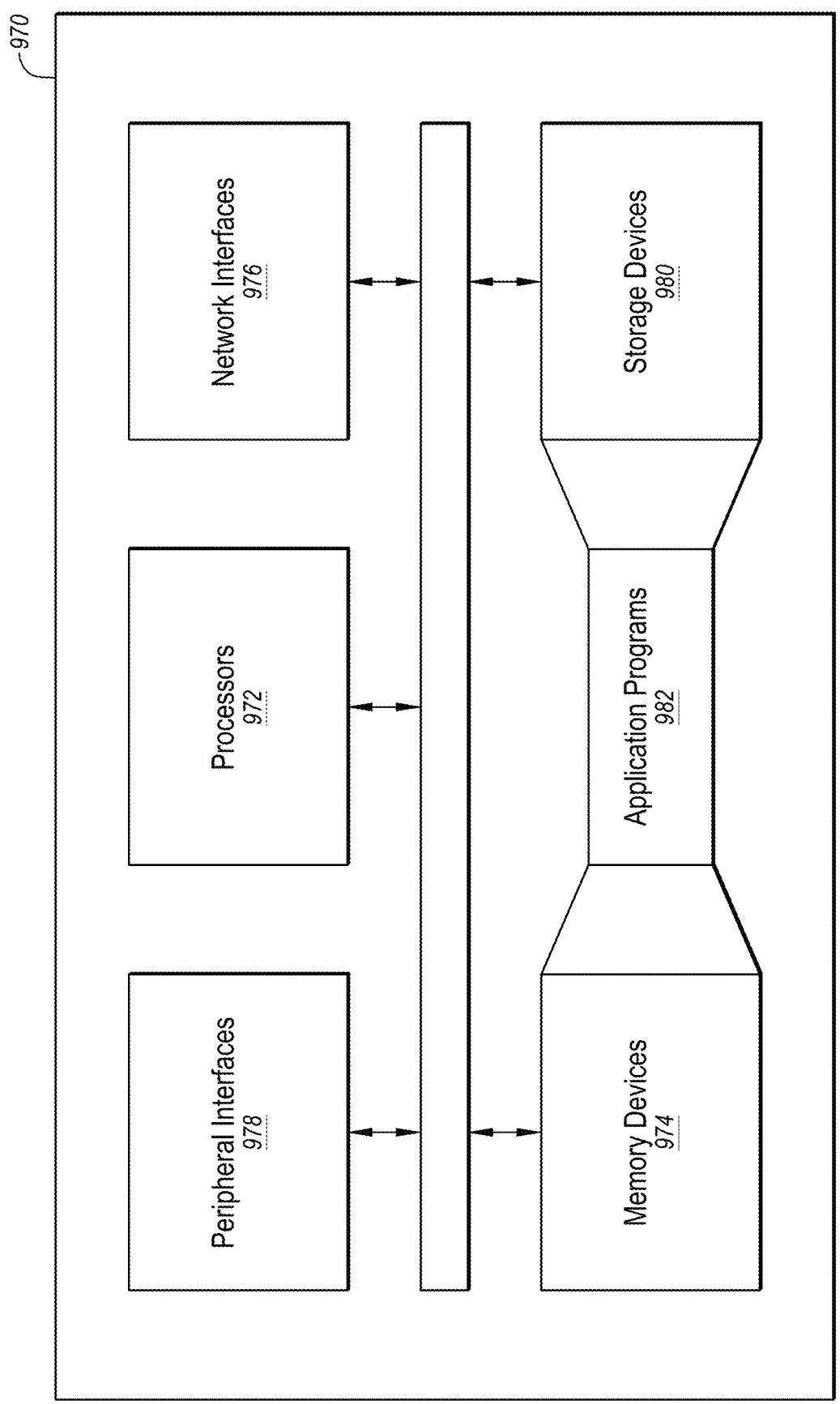
FIG. 15 depicts a system including an application program, in accordance with an embodiment of the present disclosure.

Embodiments of the disclosure may also include one or more systems for implementing one or more embodiments disclosed herein. FIG. 15 illustrates a schematic view of a processing system 970, according to an embodiment of the present disclosure. In an example, processing system 970 may be integrated within any suitable computing device. Processing system 970 may include one or more processors 972 of varying core configurations (including multiple cores) and clock frequencies. Processors 972 may be operable to execute instructions, apply logic, etc. It will be appreciated that these functions may be provided by multiple processors or multiple cores on a single chip operating in parallel and/or communicably linked together. In at least one embodiment, processors 972 may comprise and/or include one or more GPUs.

Processing system 900 may also include a memory system, which may be or include one or more memory devices and/or computer-readable media 974 of varying physical dimensions, accessibility, storage capacities, etc. such as flash drives, hard drives, disks, random access memory, etc., for storing data, such as images, files, and program instructions for execution by processors 974. In an embodiment, computer-readable media 974 may store instructions that, when executed by processors 972, are configured to cause processing system 970 to perform operations. For example, execution of such instructions may cause processing system 970 to implement one or more embodiments described herein.

Processing system 970 may also include one or more network interfaces 976, which may include any hardware, applications, and/or other software. Accordingly, network interfaces 976 may include Ethernet adapters, wireless transceivers, PCI interfaces, and/or serial network components, for communicating over wired or wireless media using protocols, such as Ethernet, wireless Ethernet, etc.

Processing system 970 may further include one or more peripheral interfaces 978, for communication with a display screen, projector, keyboards, mice, touchpads, sensors, other types of input and/or output peripherals, and/or the like. In some implementations, the components of processing system 970 need not be enclosed within a single enclosure or even located in close proximity to one another, but in other implementations, the components and/or others may be provided in a single enclosure.

Memory device 974 may be physically or logically arranged or configured to store data on one or more storage devices 980. Storage device 980 may include one or more file systems or databases in any suitable format. Storage device 980 may also include one or more application programs 982, which may contain interpretable or executable instructions for performing one or more of the disclosed processes. When requested by processors 972, one or more of the application programs 982, or a portion thereof, may be loaded from storage devices 980 to memory devices 974 for execution by processors 972.

Those skilled in the art will appreciate that the above-described componentry is merely one example of a hardware configuration, as the processing system 970 may include any type of hardware components, including any necessary accompanying firmware or software, for performing the disclosed implementations. Processing system 970 may also be implemented in part or in whole by electronic circuit components or processors, such as application-specific integrated circuits (ASICs) or field-programmable gate arrays (FPGAs).

Although the foregoing description contains many specifics, these should not be construed as limiting the scope of the disclosure or of any of the appended claims, but merely as providing information pertinent to some specific embodiments that may fall within the scopes of the disclosure and the appended claims. Features from different embodiments may be employed in combination. In addition, other embodiments of the disclosure may also be devised which lie within the scopes of the disclosure and the appended claims. The scope of the disclosure is, therefore, indicated and limited only by the appended claims and their legal equivalents. All additions, deletions and modifications to the disclosure, as disclosed herein, that fall within the meaning and scopes of the claims are to be embraced by the claims.

What is claimed:

1. A method comprising:
receiving a plurality of images including a first image from a first medical image modality and including a first ontological code and a second image from a second medical image modality and including a second ontological code, at least one of the first ontological code and the second ontological code including a billing code, the first medical image modality being different from the second medical image modality;
establishing one or more data sets including the first image and the second image, wherein the first image and the second image are assigned and share a common patient identifier;
generating a first visual annotation on the first image and a second visual annotation on the second image, the second visual annotation on the second image being semantically enabled to form a relationship with the first visual annotation on the first image using a semantic ontological framework, the first visual annotation on the first image including a first region of interest (ROI) on the first image, the generating of the first ROI on the first image including identifying the first ROI on the first image, the second visual annotation on the second image including a second ROI on the second image, the generating of the second ROI on the second image including automatically mapping the first ROI on the first image to the second image;
maintaining the relationship amongst the first image and the second image in the one or more data sets via a semantic layer of the semantic ontological framework;
rendering and displaying, in a single view, the first image with the first visual annotation simultaneously with the second image with the second visual annotation, the first image and the second image being displayed separately from but adjacent to one another; and
generating a report including one or more outputs based on the relationship.

2. The method of claim 1, wherein the first visual annotation includes a region of interest in the first image.

3. The method of claim 1, wherein the one or more outputs include a continuity of care (CCD) structure output compliant with a standardized format.

4. The method of claim 1, wherein the one or more outputs include at least one of human-readable data and machine-readable data.

5. The method of claim 1, wherein the relationship includes a field of view (FOV) relationship.

6. A system comprising:
a processor configured to receive a plurality of images including a first image from a first medical image modality and including a first ontological code and a second image from a second medical image modality and including a second ontological code, at least one of the first ontological code and the second ontological code including a billing code, the first medical image modality being different from the second medical image modality;
an aggregator coupled to the processor and configured to receive processed data from the processor, establish one or more data sets including the first image and the second image, wherein the first image and the second image are assigned and share a common patient identifier; and
an annotation service module coupled to the aggregator and configured to generate a first visual annotation on the first image and a second visual annotation on the second image, the second visual annotation on the second image being semantically enabled to form a relationship with the first visual annotation on the first image using a semantic ontological framework, the first visual annotation on the first image including a first region of interest (ROI) on the first image, the generating of the first ROI on the first image including identifying the first ROI on the first image, the second visual annotation on the second image including a second ROI on the second image, the generating of the second ROI on the second image including automatically mapping the first ROI on the first image to the second image,
wherein the processor is further configured to maintain the relationship amongst the first image and the second image in the one or more data sets via a semantic layer of the semantic ontological framework, render and display, in a single view, the first image with the first visual annotation simultaneously with the second image with the second visual annotation with the first image and the second image being displayed separately from but adjacent to one another, and generate a report including one or more outputs based on the relationship.

7. The system of claim 6, further comprising a template service module configured to generate an output based on at least one image of the plurality of images.

8. The system of claim 6, further comprising at least one organizing module coupled to the aggregator and configured to organize images for formatting.

9. The system of claim 6, further comprising at least one output for generating at least one of human-readable data and machine-readable data.

10. The system of claim 9, wherein the at least one output comprises a continuity of care (CCD) structure output compliant with a standardized format.

11. A non-transitory computer-readable storage medium storing instructions that when executed by a processor cause the processor to perform instructions, the instructions comprising:
receiving a plurality of images including a first image from a first medical image modality and including a first ontological code and a second image from a second medical image modality and including a second ontological code, at least one of the first ontological code and the second ontological code including a billing code, the first medical image modality being different from the second medical image modality;
establishing one or more data sets including the first image and the second image, wherein the first image and the second image are assigned and share a common patient identifier;
generating a first visual annotation on the first image and a second visual annotation on the second image, the second visual annotation on the second image being semantically enabled to form a relationship with the first visual annotation on the first image using a semantic ontological framework, the first visual annotation on the first image including a first region of interest (ROI) on the first image, the generating of the first ROI on the first image including identifying the first ROI on the first image, the second visual annotation on the second image including a second ROI on the second image, the generating of the second ROI on the second image including automatically mapping the first ROI on the first image to the second image;

maintaining the relationship amongst the first image and the second image in the one or more data sets via a semantic layer of the semantic ontological framework;

rendering and displaying, in a single view, the first image with the first visual annotation simultaneously with the second image with the second visual annotation, the first image and the second image being displayed separately from but adjacent to one another; and generating a report including one or more outputs based on the relationship.

12. The non-transitory computer readable storage medium of claim 11, wherein the first visual annotation includes a region of interest in the first image.

13. The non-transitory computer readable storage medium of claim 11, wherein the one or more outputs include a consolidated-clinical document architecture (C-CDA) standard output.

14. The method of claim 1, wherein:

the first medical image modality is an ultrasound image modality, a progesterone receptor (PR) image modality, a magnetic resonance imaging (MRI) image modality, a human epidermal growth factor receptor (HER2) image modality, a positron emission tomography and computation tomography (PET/CT) image modality, a Hematoxylin-Eosin (H&E) image modality, an Immunohistochemistry (IHC) image modality, or a Fluorescence In Situ Hybridization (FISH) image modality; and the second medical image modality is an ultrasound image modality, a PR image modality, an MRI image modality, an HER2 image modality, a PET/CT image modality; an H&E image modality, an IHC image modality, or a FISH image modality.

* * * * *